US012257331B2

United States Patent
Khine et al.

(10) Patent No.: US 12,257,331 B2
(45) Date of Patent: Mar. 25, 2025

(54) METHODS FOR OXIDATIVELY BLEACHING OR COLORING HAIR WITHOUT DAMAGING THE HAIR

(71) Applicant: L'OREAL, Paris (FR)

(72) Inventors: Cho-Cho Khine, Scotch Plains, NJ (US); Ronak Rughani, Edison, NJ (US)

(73) Assignee: L'OREAL, Paris (FR)

( * ) Notice: Subject to any disclaimer, the term of this patent is extended or adjusted under 35 U.S.C. 154(b) by 9 days.

(21) Appl. No.: 18/355,533

(22) Filed: Jul. 20, 2023

(65) Prior Publication Data

US 2025/0064698 A1 Feb. 27, 2025

(51) Int. Cl.
*A61Q 5/10* (2006.01)
*A61K 8/362* (2006.01)
*A61Q 5/06* (2006.01)

(52) U.S. Cl.
CPC ............ *A61K 8/362* (2013.01); *A61Q 5/06* (2013.01); *A61Q 5/10* (2013.01); *A61K 2800/4322* (2013.01); *A61K 2800/48* (2013.01); *A61K 2800/5426* (2013.01)

(58) Field of Classification Search
CPC ............ A61K 8/362; A61K 2800/4322; A61K 2800/48; A61Q 5/06; A61Q 5/10
USPC .......................................................... 8/405
See application file for complete search history.

(56) References Cited

U.S. PATENT DOCUMENTS

| 5,830,440 A | 11/1998 | Sturla et al. |
| 5,846,550 A | 12/1998 | Perrin et al. |
| 6,361,782 B1 | 3/2002 | Chevalier et al. |
| 6,991,782 B2 | 1/2006 | Kanji et al. |
| 7,087,221 B2 | 8/2006 | Royce et al. |
| 7,413,580 B2 | 8/2008 | Bordier et al. |

(Continued)

FOREIGN PATENT DOCUMENTS

| BR | PI0804624 A2 | 7/2010 |
| EP | 2953610 A1 | 12/2015 |

(Continued)

OTHER PUBLICATIONS

Preliminary Search Report and Written Opinion issued on Apr. 15, 2024 for corresponding French Application No. FR 2310335.

(Continued)

*Primary Examiner* — Eisa B Elhilo
(74) *Attorney, Agent, or Firm* — POLSINELLI PC

(57) ABSTRACT

The present disclosure is drawn to methods for oxidatively bleaching or coloring hair. The methods employ a fortifying composition and a conditioning composition, which are used in various routines. Treating hair according to the routines prevent, minimize, or mitigate damage to the hair caused by the oxidative bleaching or coloring process. The fortifying composition includes: (a) citric acid, a salt thereof, or a combination thereof; (b) cyclodextrin, a salt thereof, or a combination thereof; (c) one or more polyols; and (d) water. The conditioning composition includes: (a) one or more cationic surfactants; (b) one or more non-silicone fatty compounds; (c) one or more silicone oils; and (d) and water. The methods strengthen the hair, improve curl retention of the hair, prevent frizz of the hair, and remediate damage to the hair caused by chemical bleaching or coloring of the hair.

20 Claims, 2 Drawing Sheets

(56) References Cited

U.S. PATENT DOCUMENTS

| | | |
|---|---|---|
| 8,025,701 B2 | 9/2011 | De Boni |
| 9,295,632 B1 | 3/2016 | Benn et al. |
| 9,750,678 B2 | 9/2017 | Benn |
| 9,872,824 B2 | 1/2018 | Kadir et al. |
| 10,064,799 B2 | 9/2018 | Washington et al. |
| 10,376,459 B2 | 8/2019 | Saquet-Gouville et al. |
| 10,434,051 B2 | 10/2019 | Washington et al. |
| 10,624,830 B2 | 4/2020 | Deng et al. |
| 10,813,854 B2 | 10/2020 | Arnaud et al. |
| 11,246,392 B2 | 2/2022 | Baldo |
| 11,246,823 B2 | 2/2022 | Greaves et al. |
| 11,540,997 B2 | 1/2023 | Farran et al. |
| 11,679,069 B2 | 6/2023 | Safouane et al. |
| 2005/0166336 A1 | 8/2005 | De La Mettrie |
| 2005/0169856 A1 | 8/2005 | Grollier |
| 2005/0169871 A1 | 8/2005 | De La Mettrie |
| 2005/0169872 A1 | 8/2005 | De La Mettrie |
| 2005/0169876 A1 | 8/2005 | De La Mettrie |
| 2005/0169877 A1 | 8/2005 | Grollier et al. |
| 2005/0169945 A1 | 8/2005 | De La Mettrie |
| 2005/0170023 A1 | 8/2005 | De La Mettrie |
| 2005/0175652 A1 | 8/2005 | Grollier et al. |
| 2005/0175653 A1 | 8/2005 | Grollier et al. |
| 2005/0175717 A1 | 8/2005 | De La Mettrie et al. |
| 2006/0286050 A1 | 12/2006 | Yu et al. |
| 2008/0075681 A1 | 3/2008 | Cassier et al. |
| 2008/0279803 A1 | 11/2008 | Kainz et al. |
| 2011/0243867 A1 | 10/2011 | Patel et al. |
| 2012/0258055 A1 | 10/2012 | Gray et al. |
| 2013/0261093 A1 | 10/2013 | Brieva et al. |
| 2013/0319462 A1 | 12/2013 | Cifelli |
| 2014/0057991 A1 | 2/2014 | Chevalier et al. |
| 2015/0209243 A1 | 7/2015 | Shiroya et al. |
| 2016/0008257 A1 | 1/2016 | Zhou et al. |
| 2019/0159990 A1 | 5/2019 | Guimont et al. |
| 2019/0350830 A1 | 11/2019 | Burckbuchler et al. |
| 2020/0069544 A1 | 3/2020 | Guimont et al. |
| 2020/0268641 A1 | 8/2020 | Feng et al. |
| 2021/0196591 A1 | 7/2021 | Venture Morris et al. |
| 2021/0386658 A1 | 12/2021 | Frushour et al. |
| 2022/0000727 A1 | 1/2022 | Paulucci et al. |
| 2022/0202691 A1 | 6/2022 | Saini et al. |
| 2022/0354761 A1 * | 11/2022 | Khine .................. A61K 8/362 |
| 2023/0190613 A1 | 6/2023 | Saini et al. |

FOREIGN PATENT DOCUMENTS

| | | |
|---|---|---|
| FR | 3126618 A1 | 3/2023 |
| WO | 2012084337 A2 | 6/2012 |
| WO | 2014123805 A1 | 8/2014 |
| WO | 2016090247 A1 | 6/2016 |
| WO | 2022232666 A1 | 11/2022 |

OTHER PUBLICATIONS

Database GNPD [Online]; MINTEL Anonymous:"Travel Kit," 2017 XP093016427.

Database GNPD [Online]; MINTEL Anonymous:"Permanent Hair Dye Powder," 2016 XP055655486.

* cited by examiner

METHODS FOR OXIDATIVELY BLEACHING OR COLORING HAIR WITHOUT DAMAGING THE HAIR

FIELD OF THE DISCLOSURE

The present disclosure relates to methods for oxidatively bleaching or coloring hair that prevent or minimize damage to the hair. The oxidative bleaching or coloring of the hair is carried out in a routine using a fortifying composition and a conditioning composition.

BACKGROUND

Many consumers use cosmetic and care compositions to enhance the appearance of hair, e.g., by changing the color, style, or shape of the hair and/or by imparting various cosmetic properties to hair, such as shine and conditioning. Hair can become dry or damaged for various reasons, e.g., weather exposure, poor nutrition, mechanical treatments (e.g., brushing hair), styling treatments using chemicals, dying, heat, nutrition, etc. Even cleansing products can remove hair's natural oils causing dryness, which can lead to a dull appearance, split ends, and frizz.

Chemical treatments for hair include bleaching and coloring treatments to change the color the hair. Chemical treatments also include processes to permanently change the shape and structure of the hair, for example by perming, waving, relaxing or straightening the hair. These chemical treatments change the look of hair by changing its physical structure, which inevitably causes a certain degree of damage to the hair. Environmental factors, such as salt water, sunlight, and heat, are also known to damage hair. Damaged hair is characterized by unnatural changes to the protein structure of the individual hair strands or shafts.

The popularity and usage of oils for hair treatments has increased due to their effectiveness and simplicity. Commonly used oils include olive oil, mineral oil, avocado oil, apricot kernel oil, rice bran oil, and coconut oil. However, these treatments can leave the hair feeling greasy. In addition, the effects are not usually seen after more than several hours (e.g., 8 hours) of treatment and several treatments are usually required, making it time consuming and labor intensive.

Damage to hair results in split ends, dryness, hair that is easily broken, and hair that becomes "frizzy" and unmanageable. Because the visible portion of hair is dead, it has no ability to regenerate itself. There are numerous over the counter and salon treatments that purport to repair damaged hair. These include conditioners, hot oil treatments, hydrolyzed proteins, vitamin formulations, and exotic fruit, leaf, or root extracts. These treatments, however, provide only limited improvement to the hair. Therefore, hair treatment technologies that can straighten, relax, or style the hair without chemically damaging the hair are desired.

There is still a need to remediate the damage caused to hair caused by the oxidative bleaching or coloring process.

SUMMARY OF THE DISCLOSURE

The present disclosure is drawn to methods for oxidatively bleaching or coloring hair. The methods are based on routines using a fortifying composition and a conditioning composition in conjunction with the oxidative bleaching or coloring process. The inventors discovered that using the fortifying composition and the conditioning composition in the claimed routines not only conditions the hair, but surprisingly improves physical and mechanical properties, and thermal integrity of the hair fibers, and the improvements are statistically significant. For example, the methods dramatically improve hair fiber elasticity, strength, and resistance to frizz, as illustrated by statistically significant increases in elastic modulus, break stress, and thermal integrity.

The fortifying composition and the conditioning composition are used in a pre-treatment routine or a post-treatment routine when oxidatively bleaching or coloring hair. The fortifying composition typically includes
 (a) citric acid, a salt thereof, or a combination thereof;
 (b) cyclodextrin, a derivative thereof, or a combination thereof;
  wherein a combined total amount of (a) and (b) is about 2 to about 15 wt. %, based on a total weight of the fortifying composition;
 (c) one or more polyols having from 2 to 10 carbon atoms; and
 (d) water.

The fortifying composition may have a pH of about 2 to about 6, preferably about 2 to about 5. Further, the citric acid, salt thereof, or combination thereof of (a) and cyclodextrin, derivative thereof, or combination thereof of (b) are typically in a mole ratio of about 20:1 to about 3:1 ((a):(b)) and/or a weight ratio of about 8:1 to about 1:2((a):(b)).

Citric acid and its salts provide a myriad of benefits to hair. For example, it acts as an antioxidant, removes build-up and debris from the hair, and improves blood circulation in the scalp, which in turn nourishes hair follicles and promotes growth. Its acidic pH is also useful for balancing the pH of the scalp, as many hair care products make it more alkaline. The citric acid in the instant fortifying compositions also interacts with cyclodextrin in a unique manner and improves film formation on the hair, which is further potentiated with heat. Sodium citrate (or trisodium citrate) is an example of a salt of citric acid.

Cyclodextrins are a family of cyclic oligosaccharides, comprised of a macrocyclic ring of glucose subunits joined by α-1,4 glycosidic bonds. Cyclodextrins are produced from starch by enzymatic conversion. Typical cyclodextrins contain glucose monomers ranging from six to eight units in a ring, creating a cone shape, for example, α (alpha)-cyclodextrin gas 6 glucose subunits, β (beta)-cyclodextrin has 7 glucose subunits, and γ (gamma)-cyclodextrin has 8 glucose subunits. Nonlimiting examples of cyclodextrins for use in the fortifying compositions of the present disclosure include α-cyclodextrin, ß-cyclodextrin, γ-cyclodextrin, methyl-α-cyclodextrin, methyl-ß-cyclodextrin, methyl-γ-cyclodextrin, and mixtures thereof.

Preferably, the citric acid, salt thereof, or combination thereof and the cyclodextrin, salt thereof, or combination thereof are in an association with one another. This can be accomplished by independently combining the citric acid, salt thereof, or combination thereof and the cyclodextrin, salt thereof, or combination thereof prior to addition to other components of the fortifying composition. For example, the cyclodextrin, derivative thereof, or combination thereof is preferably solubilized in the citric acid to form a solubilized combination of citric acid and cyclodextrin, derivative thereof, or combination thereof. The combination can be heated to facilitate or hasten the dissolution of the cyclodextrin. The solubility of cyclodextrin in water is not always ideal. Therefore, combining the cyclodextrin with the citric acid and dissolving the cyclodextrin in citric acid before adding the combination with other components of the fortifying composition can be beneficial.

Nonlimiting examples of polyols having from 2 to 10 carbon atoms include ethylene glycol, propylene glycol, butylene glycol, hexylene glycol, pentylene glycol, 1,3-propanediol, diethylene glycol, dipropylene glycol, caprylyl glycol, and glycerin. In various embodiments, at least one of the one or more polyols is glycerin.

In various embodiments, the fortifying composition includes one or more cationic polysaccharides. Nonlimiting examples of cationic polysaccharides include cationic guar and derivatives thereof, cationic cellulose and derivatives thereof, cationic starch and derivatives thereof, cationic callose and derivatives thereof, cationic xylan and derivatives thereof, cationic mannan and derivatives thereof, cationic galactomannan and derivatives thereof, and combinations thereof.

In various embodiments, the fortifying composition includes one or more polar oils. The polar oils can be volatile or non-volatile. Nonlimiting examples of non-volatile polar oils include hydrocarbon-based oils of plant origin such as heptanoic or octanoic triglycerides, wheatgerm oil, sunflower oil, grapeseed oil, sesame oil, corn oil, apricot oil, castor oil, camelina oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, and combinations thereof.

In various embodiments, the fortifying composition includes one or more nonionic surfactant or emulsifiers. Nonlimiting examples include alkoxylated fatty alcohols, fatty acid esters of polyoxyethylene glycol, ethoxylated mono or diglycerides, sorbitan esters, ethoxylated sorbitan esters, fatty acid glycol esters, ethylene oxide, alkyl(ether) phosphates, alkylpolyglucosides, and mixtures thereof. In various embodiments, at least one of the one or more nonionic surfactants or emulsifiers is alkoxylated, preferably ethoxylated. Nonlimiting examples include straight chain primary alcohol alkoxylates, straight chain secondary alcohol alkoxylates, alkyl phenol alkoxylates, olefinic alkoxylates, branched chain alkoxylates, fatty oil or hydrogenated fatty oil ethoxylates, alkyl sorbitan esters ethoxylates, alkyl glyceride ethoxylates, and mixtures thereof.

Nonlimiting examples of miscellaneous ingredients include preservatives, fragrances, pH adjusters, salts, chelating agents, buffers, antioxidants, flavonoids, vitamins, amino acids, botanical extracts, UV filtering agents, peptides, proteins, protein hydrolysates, and/or isolates, fillers (e.g., organic and/or inorganic fillers such as talc, calcium carbonate, silica, particular materials, etc.), emollients, composition colorants, or a mixture thereof.

The conditioning composition typically includes:
(a) one or more cationic surfactants;
(b) one or more non-silicone based fatty compounds;
(c) one or more silicones; and
(d) water.

Additionally, in various embodiments, the conditioning composition includes one or more of: (e) one or more thickening agents; (f) one or more water soluble solvents; and (g) one or more miscellaneous ingredients.

Nonlimiting examples of cationic surfactants include cetrimonium chloride, stearimonium chloride, behentrimonium chloride, cetrimonium methosulfate, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palm itamidopropyl dimethylamine, and a combination thereof.

Nonlimiting examples of non-silicone fatty compounds include oils, fatty alcohols, fatty acids, fatty esters, propylene glycol fatty acid esters, fatty carbonates, polyolefins (such as petrolatum), waxes, squalane, squalene, hydrogenated polyisobutene, hydrogenated polydecene, polybutene, mineral oil, pentahydrosqualene, plant and/or vegetable oil, hydrocarbon-based oils (such as isohexadecane), triglycerides, or a mixture thereof.

In various embodiments, at least one of the one or more non-silicone fatty compounds is a fatty alcohol. Nonlimiting examples of fatty alcohols include those having at least 8 carbon atoms and are linear or branched. In various embodiments, the one or more fatty alcohols have from 10 to 30 carbon atoms, preferably from 12 to 28 carbon atoms, for example, capryl alcohol, pelargonic alcohol, decyl alcohol, undecyl alcohol, lauryl alcohol, tridecyl alcohol, myristyl alcohol, pentadecyl alcohol, cetyl alcohol, palmitoleyl alcohol, isostearyl alcohol, isocetyl alcohol, heptadecyl alcohol, stearyl alcohol, cetearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, 1-nonacosanol, and myricyl alcohol.

Nonlimiting examples of silicone oils include dimethicone, dimethiconol, cyclopentasiloxane, cyclomethicone, cyclotetrasiloxane, cyclohexasiloxane, cycloheptasiloxane, decamethylcyclopentasiloxane, cyclotetrasiloxane, cyclotrisiloxane, capryldimethicone, caprylyl trimethicone, caprylyl methicone, cetearylmethicone, hexadecylmethicone, hexylmethicone, lauryl methicone, myristyl methicone, phenyl methicone, stearyl methicone, stearyl dimethicone, behenyl dimethicone, trifluoropropyl methicone, cetyl dimethicone, polyphenylmethylsiloxane, dimethylpolysiloxane, methylphenylpolysiloxane, methyltrimethicone, diphenylsiloxyphenyl trimethicone, and phenyl trimethicone, amino-functionalized silicones, and mixtures thereof.

In certain embodiments, at least one of the one or more silicones is an amino-functionalized silicone. Nonlimiting examples of amino-functionalized silicones include aminopropyl dimethicone, amodimethicone, bis-hydroxy/methoxy amodimethicones, bis-cetearyl amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. Aminopropyl dimethicone and amodimethicone are particularly preferred amino-functionalized silicones.

In various embodiments, the conditioning composition includes one or more thickening agents. Nonlimiting examples of thickening agents include carboxylic acid polymers, crosslinked polyacrylate polymers, polyacrylamide polymers, polyvinylpyrrolidone, polysaccharides, polysaccharide derivatives, gums, starch and starch derivatives, and a combination thereof.

The conditioning composition optionally includes one or more water soluble solvents. Nonlimiting examples of water-soluble solvents include $C_2$-$C_6$ monoalcohols, polyols (polyhydric alcohols), glycerin, glycols, or a combination thereof. The polyols preferably have two or three hydroxyl groups. Nonlimiting examples of include ethylene glycol, propylene glycol, butylene glycol, hexylene glycol, pentylene glycol, 1,3-propanediol, diethylene glycol, dipropylene glycol, caprylyl glycol, glycerin, and a combination thereof.

Nonlimiting examples of miscellaneous ingredients include preservatives, fragrances, pH adjusters, salts, chelating agents, buffers, antioxidants, flavonoids, vitamins, amino acids, botanical extracts, UV filtering agents, peptides, proteins, protein hydrolysates, and/or isolates, fillers (e.g., organic and/or inorganic fillers such as talc, calcium carbonate, silica, particular materials, etc.), emollients, composition colorants, or a mixture thereof.

As noted earlier, the fortifying composition and the conditioning composition can be used in a pre-treatment routine or a post-treatment routine. With the pre-treatment routine, the fortifying composition is applied to the hair before oxidatively bleaching or coloring the hair and remains on the hair when an oxidative bleaching or coloring composition is applied to the hair, i.e., the fortifying composition is not rinsed from the hair prior to oxidatively bleaching or coloring the hair. Instead, the oxidative bleaching or coloring composition is "layered" onto the fortifying composition already applied to the hair. The conditioning composition, however, is applied to the hair after completion of the oxidative bleaching or coloring process. After completion of the oxidative bleaching or coloring process, the oxidative bleaching or coloring composition is removed from the hair by cleansing the hair with a shampoo. After rinsing the shampoo from the hair, the hair is treated with the conditioning composition.

As the name suggests, in the post-treatment routine, the fortifying composition is applied to the hair after oxidatively bleaching or coloring the hair. The hair is initially bleached or colored with an oxidative bleaching or coloring composition and the oxidative bleaching or coloring composition is rinsed from the hair. After rinsing the oxidative bleaching or coloring composition from the hair, the hair is treated with a first application of the fortifying composition. After treatment with the first application of the fortifying composition, the hair is cleansed with a shampoo. There is no need to rinse the first application of the fortifying composition from the hair prior to cleansing with a shampoo. After rinsing the shampoo from the hair, the hair is treated with a second application of the fortifying composition. Subsequently, without rinsing the second application of the fortifying composition from the hair, the conditioning composition is applied to the hair, i.e., the conditioning composition is layered onto the fortifying composition, which is already applied to the hair. Upon completing treatment with the conditioning composition, the fortifying composition and the conditioning composition are rinsed from the hair.

The methods described above and throughout the disclosure protect the hair from damage due to oxidative bleaching or coloring, strengthen the hair, improve curl retention of the hair, prevent frizz of the hair, and/or remediate damage to the hair caused by chemical bleaching or coloring of the hair.

BRIEF DESCRIPTION OF FIGURES

Implementation of the present technology will now be described, by way of example only, with reference to the attached figures, wherein.

DETAILED DESCRIPTION OF THE DISCLOSURE

Figure 1:
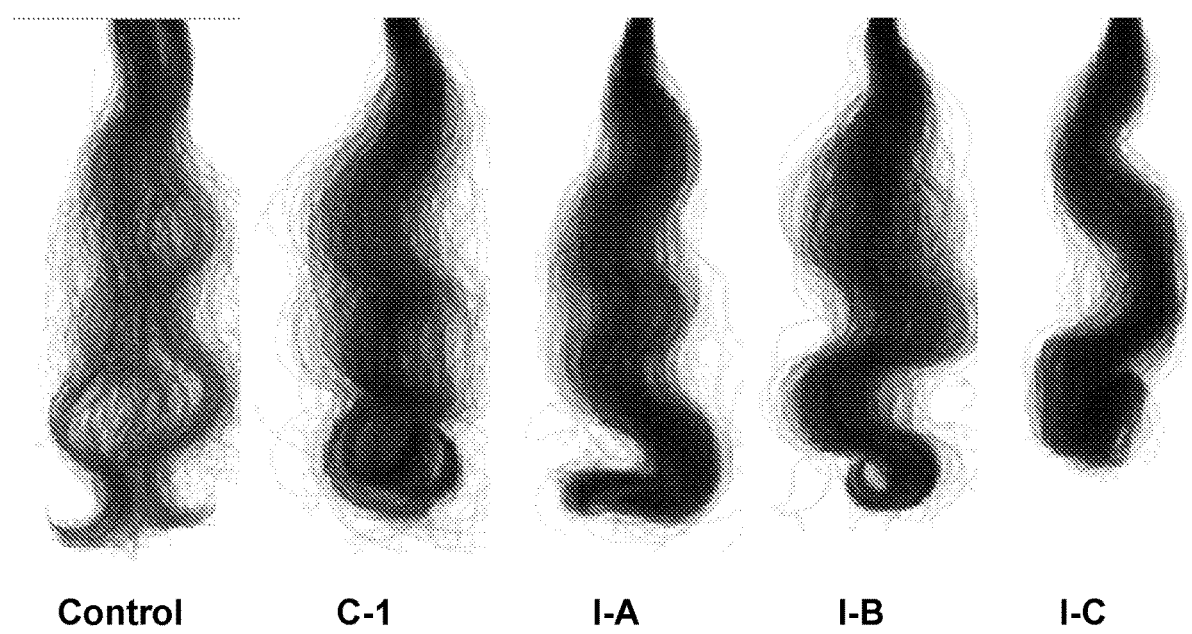
FIG. 1 shows hair swatches treated according to the instant disclosure and hair swatches treated with comparative routines after being subjected to a humidity treatment.

A fortifying composition and a conditioning composition are used in the methods of the instant disclosure to prevent or minimize damage to hair subjected to an oxidative bleaching or coloring procedure. The fortifying composition can be applied before oxidatively bleaching or coloring the hair (as a pre-treatment) or the fortifying composition can also be applied to the hair after oxidatively bleaching or coloring the hair (as a post-treatment). The inventors discovered that using the fortifying composition and the conditioning composition according to the routines set forth herein surprisingly improves physical properties of hair fibers, and the improvements are statistically significant. Specifically, hair treated according to the methods of the instant case show statically significant improvements for elasticity, break stress (strength), and thermal integrity. In addition, hair treated according to the instant disclosure show greater resistance to frizz under high humidity conditions, which may be due, at least in part, to the improved elasticity, break stress, and thermal integrity.

In accordance with the pre-treatment routine, a fortifying composition is applied to the hair before oxidatively bleaching or coloring the hair. The fortifying composition is applied to the hair and remains on the hair for a first period of time. Upon completion of treatment with the fortifying composition (upon expiration of the first period of time), an oxidative bleaching or coloring composition is layered onto the hair, upon which the fortifying composition is already applied. The fortifying composition is not rinsed from the hair prior to application of the oxidative bleaching or coloring composition. The oxidative bleaching or coloring composition remains on the hair for a time sufficient to achieve a desired degree of bleaching or coloring, at which point the bleaching or coloring composition is removed from the hair by cleansing and rinsing the hair with a shampoo. After rinsing the shampoo from the hair, the conditioning composition is applied to the hair and remains on the hair for second period of time. Upon completion of treatment with the conditioning composition (upon expiration of the second period of time), the conditioning composition is rinsed from the hair. The hair may be dried and/or styled, if desired.

In accordance with the post-treatment routine, a fortifying composition is not required before oxidatively bleaching or coloring the hair. In the post-treatment routine, the hair is bleached or colored with an oxidative bleaching or coloring composition. The oxidative bleaching or coloring composition remains on the hair for a time sufficient to achieve a desired degree of bleaching or coloring, at which point the bleaching or coloring composition is removed from the hair by cleansing and rinsing the hair with a shampoo. After rinsing the shampoo from the hair, the hair is treated with a first application of the fortifying composition for a first period of time. Upon completion of treatment with the first application of the fortifying composition (upon expiration of the first period of time), the hair is cleansed with a shampoo and the shampoo is rinsed from the hair. After rinsing the shampoo from the hair, the hair is treated with a second application of the fortifying composition for a second period of time. Upon completion of treatment with the second application of the fortifying composition (upon expiration of the second period of time), without rinsing the second application of the fortifying composition from the hair, the conditioning composition is applied to the hair, i.e., the conditioning composition is layered onto the fortifying composition, which is already applied to the hair. The conditioning composition remains on the hair for a third period of time. Upon completion of treatment with the conditioning composition (upon expiration of the third period of time), the fortifying composition and the conditioning composition are rinsed from the hair. The hair can subsequently be dried and/or styled, if desired.

A more detailed discussion of the pre-treatment routine and the post-treatment routine is described under the heading "Methods." Details of the fortifying composition and the conditioning composition follows.

Fortifying Composition (a) Citric Acid and Salts Thereof

The total amount of citric acid, salts thereof, or combination thereof will vary. Nonetheless, in various embodiments, the fortifying composition includes about 1 to about 5 wt. % of citric acid, salts thereof, or a combination thereof, based on a total weight of the composition. In further embodiments, the fortifying composition includes about 1 to about 4 wt. %, about 1 to about 3 wt. %, about 2 to about 5 wt. %, about 2 to about 4 wt. %, about 2 to about 3 wt. %, about 2.5 to about 5 wt. %, about 2.5 to about 4 wt. %, about 2.5 to about 3 wt. %, or about 1, about 1.5, about 2, about 2.5, about 3, about 3.5, about 4, about 4.5, or about 5 wt. % of citric acid, salts thereof, or a combination thereof, based on a total weight of the fortifying composition.

(b) Cyclodextrin and Derivatives

Fortifying compositions according to the disclosure include at least one cyclodextrin or derivative thereof. As used herein, the term "cyclodextrins" includes slats of carboxylic acid, whether or not expressly stated. Cyclodextrins are a family of cyclic oligosaccharides consisting of a macrocyclic ring of glucose subunits joined by α-1,4 glycosidic bonds.

The cyclodextrins that can be used include those of the formula:

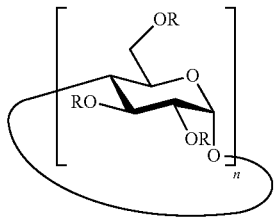

wherein:
R is chosen from H, $CH_3$, or a hydroxypropyl group, and n ranges from 6-8.

For example, in embodiments where R=H, the cyclodextrin may be α-cyclodextrin (n=6), ß-cyclodextrin (n=7), or γ-cyclodextrin (n=8). By way of example, α-cyclodextrin sold by the company WACKER under the name CAVAMAX W6 PHARMA, ß-cyclodextrin sold by the company WACKER under the name CAVAMAX W7 PHARMA, or γ-cyclodextrin sold by the company WACKER under the name CAVAMAX W8 PHARMA can be used.

In other embodiments where R=$CH_3$, the cyclodextrin may be a methyl-cyclodextrin, such as methyl-α-cyclodextrin (n=6), methyl-ß-cyclodextrin (n=7), or methyl-γ-cyclodextrin (n=8). For example, the methyl-ß-cyclodextrin sold by the company WACKER under the name CAVASOL W7 may be chosen.

In various embodiments, the at least one cyclodextrin may comprise a mixture of cyclodextrins and/or derivatives thereof. For example, the at least one cyclodexctrin may be a mixture of α-cyclodextrin, ß-cyclodextrin, and/or γ-cyclodextrin. In another embodiment, the at least one cyclodextrin includes ß-cyclodextrin. In yet a further embodiment, the cyclodextrin is only ß-cyclodextrin, and no other cyclodextrins or derivatives thereof are present in the fortifying composition.

In one embodiment, the fortifying compositions according to the present disclosure includes ß-cyclodextrin in an amount ranging from about 0.1% to about 10%, such as from 0.2% to about 8%, from about 0.3% to about 7%, from about 0.4% to about 6%, from about 1% to about 10%, from about 1% to about 8%, from about 1% to about 5%, from about 1% to about 3% by weight, relative to the total weight of the fortifying composition.

The total amount of cyclodextrin, a derivative thereof, or combination thereof in the fortifying compositions will vary. Nonetheless, in various embodiments, the fortifying composition includes about 0.5 to about 5 wt. % of cyclodextrin, a derivative thereof, or a combination thereof, based on a total weight of the fortifying composition. In further embodiments, the fortifying composition includes 0.5 to about 4 wt. %, about 0.5 to about 3 wt. %, about 0.5 to about 2 wt. %, about 1 to about 5 wt. %, about 1 to about 4 wt. %, about 1 to about 3 wt. %, about 1 to about 2 wt. %, about 1.5 to about 5 wt. %, about 1.5 to about 4 wt. %, about 1.5 to about 3 wt. %, about 1.5 to about 2 wt. %, about 0.5 wt. %, about 1 wt. %, about 1.25 wt. %, about 1.5 wt. %, about 2 wt. %, about 2.5 wt. %, about 3 wt. %, about 3.5 wt. %, about 4 wt. %, about 4.5 wt. %, or about 5 wt. % of a cyclodextrin, a derivative thereof, or a combination thereof, based on a total weight of the fortifying composition.

Combination of Citric Acid/Salts and Cyclodextrin

The total combined amount of the citric acid, salts thereof, or combination thereof of (i)(a) and the cyclodextrin, derivative thereof, or combination thereof of (b) will vary. Nonetheless, in various embodiments the total combined amount of the citric acid, salts thereof, or combination of (i)(a) and the cyclodextrin, derivative thereof, or combination thereof of (i)(b) is about 2 to about 15 wt. %, based on a total weight of the fortifying composition. In further embodiments, the total combined amount of the citric acid, salts thereof, or combination of (i)(a) and the cyclodextrin, derivative thereof, or combination thereof of (i)(b) is about 2 to about 12 wt. %, about 2 to about 10 wt. %, about 2 to about 8 wt. %, about 2 to about 6 wt. %, about 2 to about 5 wt. %, about 3 to about 12 wt. %, about 3 to about 10 wt. %, about 3 to about 8 wt. %, about 3 to about 6 wt. %, about 3 to about 5 wt. %, or about 2 wt. %, 3 wt. %, 4 wt. %, 5 wt. %, 6 wt. %, 7 wt. %, or 8 wt. %, based on a total weight of the fortifying composition.

The weight ratio of the citric acid, salts thereof, or combination thereof of (i)(a) to the cyclodextrin, derivative thereof, or combination thereof of (i)(b) will vary. Nonetheless, in certain embodiments, the citric acid, salts thereof, or combination of (i)(a) and the cyclodextrin, derivatives thereof, or combination thereof of (i)(b) are in a weight ratio of about of about 8:1 to about 1:2((i)(a):(i)(b)). In further embodiments, the citric acid, salts thereof, or combination of (i)(a) and the cyclodextrin, derivatives thereof, or combination thereof of (i)(b) are in a weight ratio of 6:1 to about 1:2, about 5:2 to about 1:2, about 4:1 to about 1:2, about 3:1 to about 1:2, about 2:1 to about 1:2, about 8:1 to about 1:1, about 6:1 to about 1:1, about 5:1 to about 1:1, about 4:1 to about 1:1, about 3:1 to about 1:1, about 2:1 to about 1:1, about 1.2:1, about 1.3:1, about 1.4:1, about 1.5:1, about 1.6:1, about 1.7:1 or about 1.8:1 ((i)(a):(i)(b)).

The mole ratio of the citric acid, salts thereof, or combination thereof of (i)(a) to the cyclodextrin, derivative thereof, or combination thereof of (i)(b) will vary. Nonetheless, in certain embodiments, the citric acid, salts thereof, or combination thereof of (i)(a) and the cyclodextrin, derivative thereof, or combination thereof of (i)(b) are in a mole ratio of about 20:1 to about 3:1. In further embodiments, the citric acid, salts thereof, or combination of (a) and the cyclodextrin or derivatives of (b) are in a mole ratio of about 18:1 to about 3:1, about 15:1 to about 3:1, about 20:1 to about 5:1, about 18:1 to about 5:1, about 15:1 to about 5:1, about 20:1 to about 8:1, about 18:1 to about 8:1, about 15:1 to about 8:1, about 20:1 to about 10:1, about 18:1 to about 10:1, about 15:1 to about 10:1, about 14:1, about 13:1, about 12:1, about 11:1, about 10:1, about 9:1, or about 8:1.

In various embodiments, the citric acid, salts thereof, or combination of (i)(a) and the cyclodextrin, derivative thereof, or combination thereof of (i)(b) are combined with one another before being added into the fortifying composition of the instant disclosure. For example, the cyclodextrin, derivative thereof, or combination thereof is preferably solubilized in the citric acid to form a solubilized combination of citric acid and cyclodextrin. The combination can be heated to facilitate or hasten the dissolution of the cyclodextrin. The solubility of cyclodextrin in water is not always ideal. Therefore, combining the cyclodextrin with the citric acid and dissolving the cyclodextrin in citric acid before adding the combination with other components of the fortifying composition can be beneficial.

(c) Polyols Having from 2 to 10 Carbon Atoms

One or more polyols in the fortifying composition have from 2 to 10 carbon atoms. Preferably the polyols also have two or three hydroxyl groups. For example, the polyols may be selected from glycols and glycerol. Nonlimiting examples of polyols having from 2 to 10 carbon atoms include ethylene glycol, propylene glycol, butylene glycol, hexylene glycol, pentylene glycol, 1,3-propanediol, diethylene glycol, dipropylene glycol, caprylyl glycol, and glycerin.

The total amount of the one or more polyols having from 2 to 10 carbon atoms, will vary. Nonetheless, in certain embodiments, the fortifying composition includes about 0.1 wt. % to about 25 wt. % of the one or more polyols having from 2 to 10 carbon atoms, based on a total weight of the fortifying composition. In further embodiments, the fortifying composition includes about 0.1 to about 20 wt. %, about 0.1 to about 15 wt. %, about 0.1 to about 10 wt. %, about 0.1 to about 8 wt. %, about 0.1 to about 5 wt. %, about 0.1 to about 3 wt. %, about 0.5 to about 25 wt. %, about 0.5 to about 20 wt. %, about 0.5 to about 15 wt. %, about 0.5 to about 12 wt. %, about 0.5 to about 10 wt. %, about 0.5 to about 8 wt. %, about 0.5 to about 5 wt. %, about 0.5 to about 3 wt. % of the one or more polyols having from 2 to 10 carbon atoms, based on the total weight of the fortifying composition.

(d) Water

The fortifying composition typically includes a large proportion of water. The total amount of water will vary but is typically in an amount of about 50 to about 97 wt. %, based on a total weight of the fortifying composition. In certain embodiment, the fortifying composition includes about 60 to about 97 wt. %, about 70 to about 97 wt. %, about 75 to about 97 wt. %, about 80 to about 97 wt. %, about 85 to about 97 wt. %, about 90 to about 97 wt. %, about 50 to about 95 wt. %, about 60 to about 95 wt. %, about 70 to about 95 wt. %, about 75 to about 95 wt. %, about 80 to about 95 wt. %, about 85 to about 95 wt. %, about 90 to about 95 wt. % of water, based on the total weight of the fortifying composition.

(e) Cationic Polysaccharide

A cationic polysaccharide has a positive charge density, for example, from 0.01 meq/g to 20 meq/g, preferably from 0.05 to 15 meq/g, and more preferably from 0.1 to 10 meq/g. Cationic polysaccharides may have at least one positively chargeable and/or positively charged moiety selected from the group consisting of a primary, a secondary or tertiary amino group, a quaternary ammonium group, a guanidine group, a biguanide group, an imidazole group, an imino group, and a pyridyl group. The term (primary) "amino group" here means the group —$NH_2$. Examples of the quaternary ammonium groups include 3-chloro-2-hydroxypropyl trimethyl ammonium chloride (CHPTMAC), 2,3-epoxypropyl trimethyl ammonium chloride (EPTAC), diallyldimethyl ammonium chloride (DMDAAC), vinylbenzene trimethyl ammonium chloride, trimethylammonium ethyl metacrylate chloride, methacrylamidopropyltrimethyl ammonium chloride (MAPTAC), and tetraalkylammonium chloride.

It is preferable that the cationic polysaccharide have at least one quaternary ammonium group, preferably a quaternary trialkyl ammonium group, and more preferably a quaternary trimethyl ammonium group.

One example of the cationic functional group in the cationic polysaccharides, such as the cationic guars, is trimethylamino(2-hydroxyl)propyl, with a counter ion. Various counter ions can be utilized, including but not limited to halides, such as chloride, fluoride, bromide, and iodide, sulfate, notrate, methylsulfate, and mixtures thereof. In certain embodiments, the one or more cationic polysaccharides are selected from cationic guars. In other embodiments, at least one of the one or more cationic polysaccharides is a cationic guar. Guars are polysaccharides composed of the sugars galactose and mannose. The backbone is a linear chain of β 1,4-linked mannose residues to which galactose residues are 1,6-linked at every second mannose, forming short side-branches. Within the context of the present disclosure, the cationic guars may be considered cationic derivatives of guars.

Nonlimiting examples of cationic polysaccharides include cationic guars, cationic celluloses (also referred to as cationic cellulose polymers), cationic starches, cationic gums, cationic callose, cationic xylan, cationic mannan, and cationic galactomannan.

Cationic guars include cationic hydroxyalkyl guars, such as cationic hydroxyethyl guar, cationic hydroxypropyl guar, cationic hydroxybutyl guar, and cationic carboxylalkyl guars including cationic carboxymethyl guar, cationic alkylcarboxy guars such as cationic carboxylpropyl guar, cationic carboxybutyl guar, cationic carboxymethylhydroxypropyl guar. In an exemplary embodiment, the cationic guar is guar hydroxypropyltrimonium chloride, hydroxypropyl guar hydroxypropyltrimonium chloride, or a combination thereof.

The cationic polysaccharide, such as the cationic guars, may have an average Molecular Weight (Mw) of between 100,000 Daltons and 3,500,000 Daltons, preferably between 100,000 Daltons and 1,500,000 Daltons, more preferably between 100,000 Daltons and 1,000,000 Daltons.

In the context of the present application, the term "Degree of Substitution (DS)" of cationic polysaccharides, such as cationic guars, is the average number of hydroxyl groups substituted per sugar unit. DS may be determined by titration. The DS of the cationic polysaccharide, such as the cationic guar, may be in the range of 0.01 to 1. Preferably, the DS of the cationic polysaccharide, such as the cationic guar, is in the range of 0.05 to 1. More preferably, the DS of the cationic polysaccharide, such as the cationic guar, is in the range of 0.05 to 0.2.

In the context of the present application, "Charge Density (CD)" of cationic polysaccharides, such as cationic guars, means the ratio of the number of positive charges on a monomeric unit of which a polymer is comprised to the molecular weight of said monomeric unit. The CD of the cationic polysaccharide, such as the cationic guar, may be in the range of 0.1 to 3 (meq/gm). Preferably, the CD of the cationic polysaccharide, such as the cationic guar, is in the range of 0.1 to 2 (meq/gm). More preferably, the CD of the cationic polysaccharide, such as the cationic guar, is in the range of 0.1 to 1 (meq/gm).

In certain embodiments, at least one of the one or more cationic polysaccharides is a cationic cellulose (or "cationic cellulose polymer"), for example, cellulose ether derivatives comprising one or more quaternary ammonium groups. These polymers are defined in the CTFA dictionary as quaternary ammoniums of hydroxyethylcellulose that have reacted with an epoxide substituted with a trimethylammonium group. Cationic cellulose polymers include cellulose copolymers and cellulose derivatives grafted with at least one water-soluble monomer of quaternary ammonium, such as hydroxyalkylcelluloses, for instance, hydroxymethyl-, hydroxyethyl-, and hydroxypropylcelluloses grafted, for example, with at least one chosen from methacryloylethyltrimethylammonium, methacrylamidopropyltrimethylammonium, and dimethyldiallylammonium. Also useful are cationic cellulose polymers having at least one quaternary ammonium group comprising at least one fatty chain, such as alkyl, arylalkyl or alkylaryl groups comprising at least 8 carbon atoms. The cationic cellulose polymers may be quaternized hydroxyethylcelluloses modified with at least one quaternary ammonium group comprising at least one fatty chain, such as alkyl, arylalkyl or alkylaryl groups comprising at least 8 carbon atoms, or mixtures thereof. The alkyl radicals borne by the quaternary ammonium group may preferably contain from 8 to 30 carbon atoms, especially from 10 to 30 carbon atoms. The aryl radicals preferably denote phenyl, benzyl, naphthyl or anthryl groups.

In various embodiments, at least one of the one or more cationic polysaccharides may be a cationic starch. As a nonlimiting example of cationic starches, mention may be made of starches modified with a 2,3-epoxypropyltrimethylammonium salt (e.g. chloride), such as the product known as starch hydroxypropyltrimonium chloride according to the INCI nomenclature.

In various embodiments, at least one of the one or more cationic polysaccharides may be a cationic gum, for example, a cationic cassia gum, karaya gum, konjac gum, gum tragacanth, tara gum, acacia gum, or gum arabic. Nonlimiting examples of cationic gums include cationic polygalactomannan derivatives such as guar gum derivatives and cassia gum derivatives, e.g., CTFA: Guar Hydroxypropyltrimonium Chloride, Hydroxypropyl Guar Hydroxypropyltrimonium Chloride, and Cassia Hydroxypropyltrimonium Chloride.

In certain embodiments, the one or more cationic polysaccharides may include polyquaternium-4, polyquaternium-10, polyquaternium-24, polyquaternium-67, starch hydroxypropyl trimonium chloride, starch hydroxypropyltrimonium chloride, guar hydroxypropyltrimonium chloride, hydroxypropyl guar hydroxypropyltrimonium chloride, or a combination thereof.

The amount of the one or more cationic polysaccharides in the fortifying composition will vary. Nonetheless, in certain embodiments, the fortifying composition includes about 0.05 to about 5 wt. % of the one or more cationic polysaccharides. In further embodiments, the fortifying composition includes about 0.05 to about 4 wt. %, about 0.05 to about 3 wt. %, about 0.05 to about 2 wt. %, about 0.1 to about 5 wt. %, about 0.1 to about 4 wt. %, about 0.1 to about 3 wt. %, about 0.1 to about 2 wt. %, about 0.5 to about 5 wt. %, about 0.5 to about 4 wt. %, about 0.5 to about 3 wt. %, about 0.5 to about 2 wt. %, about 0.8 wt. %, about 0.9 wt. %, about 1 wt. %, about 1.1 wt. %, about 1.2 wt. %, or about 1.5 wt. % of the one or more cationic polysaccharides, based on the total weight of the fortifying composition.

(f) Polar Oils

The fortifying composition may optionally comprise one or more polar oils.

The term "oil" is intended to mean any fatty substance that is in liquid form at room temperature (25° C.) and at atmospheric pressure. Nonlimiting examples of oils include volatile oils and non-volatile oils, which may be hydrocarbon-based oils, especially of animal or plant origin, synthetic oils, silicone oils, fluoro oils, or mixtures thereof.

For the purposes of the present invention, "silicone oil" is intended to mean an oil comprising at least one silicon atom, and especially at least one Si—O group.

"Hydrocarbon-based oil" is intended to mean an oil mainly containing hydrogen and carbon atoms and optionally oxygen, nitrogen, sulphur and/or phosphorus atoms.

The one or more polar oils may include non-silicone polar oils, silicone polar oils, or a combination thereof.

For the purposes of the present invention, "polar oil" is intended to mean an oil of which the solubility parameter $\delta_a$ at 25° C. is other than 0 $(J/cm^3)^{1/2}$. In particular, "polar oil" is intended to mean an oil of which the chemical structure is formed essentially from, or even constituted of, carbon and hydrogen atoms, and comprising at least one highly electronegative heteroatom such as an oxygen, nitrogen, silicon or phosphorus atom. The definition and calculation of the solubility parameters in the Hansen three-dimensional solubility space are described in the article by C. M. Hansen: *The three-dimensional solubility parameters*, J. PAINT TECHNOL., 39, 105 (1967), which is incorporated herein by reference in its entirety. According to this Hansen space:

$\delta_D$ characterizes the London dispersion forces resulting from the formation of dipoles induced during molecular impacts;

$\delta_P$ characterizes the Debye interaction forces between permanent dipoles and also the Keesom interaction forces between induced dipoles and permanent dipoles;

$\delta_h$ characterizes the forces of specific interactions (such as hydrogen bonds, acid/base bonds, donor/acceptor bonds, and the like);

$\delta_a$ is determined by the equation: $\delta_a = (S_p^2 + \delta_h^2)^{1/2}$.

The parameters $\delta_P$, $\delta_h$, $\delta_D$ and $\delta_a$ are expressed as $(J/cm^3)^{1/2}$.

Preferably, the one or more polar oils have a $\delta_a$ of between 4 and 9.1, preferably a $\delta_a$ of between 6 and 9.1, even better still between 7.3 and 9.1.

(i) Non-Volatile Polar Oils

The term, "non-volatile oil" is intended to mean an oil having a vapour pressure of less than 0.13 Pa (0.01 mmHg). The non-volatile oils may be chosen especially from non-volatile hydrocarbon-based oils, which may be fluorinated, and/or non-volatile silicone oils. Nonlimiting examples of non-volatile hydrocarbon-based oils include:

Hydrocarbon-based oils of animal origin,

Hydrocarbon-based oils of plant origin such as phytostearyl esters, such as phytostearyl oleate, phytostearyl isostearate and lauroyl/octyldodecyl/phytostearyl glutamate, for example sold under the name Eldew PS203® by Ajinomoto, triglycerides constituted of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, camelina oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides.

Synthetic esters, such as the oils of formula $R_1COOR_2$, in which $R_1$ represents the residue of a linear or branched fatty acid comprising from 1 to 40 carbon atoms and $R_2$ represents an especially branched hydrocarbon-based chain containing from 1 to 40 carbon atoms, with the proviso that $R_1+R_2$ is $\geq 10$. The esters may be chosen especially from fatty acid esters, polyol esters and pentaerythrityl esters, esters of diol dimers, and esters of diacid dimers, Nonlimiting examples of fatty acid esters include cetostearyl octanoate, esters of isopropyl alcohol and of C8-C18, preferably C12-C16 fatty acids, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;

Nonlimiting examples of polyol esters and pentaerythrityl esters include dipentaerythrityl tetrahydroxystearate/tetraisostearate;

Fatty alcohols that are liquid at room temperature, with a branched and/or unsaturated carbon-based chain having from 12 to 26 carbon atoms, preferably 6 to 22 carbon atoms, even better still from 18 to 20 carbon atoms, such as 2-octyldodecanol, isostearyl alcohol, oleyl alcohol, 2-hexyldecanol, 2-butyloctanol and 2-undecylpentadecanol, Higher fatty acids such as oleic acid, linoleic acid and linolenic acid, and mixtures thereof;

Dialkyl carbonates, the two alkyl chains possibly being identical or different, such as the dicaprylyl carbonate, Diesters of $C_2$-$C_{16}$, preferably $C_8$-$C_{12}$ dicarboxylic acid and of $C_1$-$C_4$ monoalcohol, preferably of branched $C_3$-$C_4$ monoalcohol. Preferably, the diester of sebacic acid and of isopropyl alcohol, such as the diisopropyl sebacat, Non-volatile silicone oils, such as, for example, non-volatile polydimethylsiloxanes (PDMSs), polydimethylsiloxanes comprising alkyl or alkoxy groups that are pendent and/or at the end of a silicone chain, these groups each containing from 2 to 24 carbon atoms, phenyl silicones, such as phenyl trimethicones, phenyl dimethicones, phenyltrimethylsiloxydiphenylsiloxanes, diphenyl dimethicones, diphenylmethyldiphenyltrisiloxanes and 2-phenylethyltrimethylsiloxysilicates, and dimethicones or phenyl trimethicones with a viscosity of less than or equal to 100 cSt, and mixtures thereof.

(ii) Volatile Polar Oils

The term, "volatile oil" is intended to mean an oil (or non-aqueous medium) that is capable of evaporating on contact with the skin in less than one hour, at ambient temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa (10-3 to 300 mmHg), in particular ranging from 1.3 Pa to 13 000 Pa (0.01 to 100 mmHg) and more particularly ranging from 1.3 Pa to 1300 Pa (0.01 to 10 mmHg).

Nonlimiting examples of volatile polar oils include volatile linear or cyclic silicone oils, especially those having a viscosity 8 centistokes ($8 \times 10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. More specific nonlimiting examples of volatile silicone oils include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and combinations thereof. Volatile fluoro oils such as nonafluoromethoxybutane or perfluoromethylcyclopentane, and mixtures thereof, may also be used.

According to a preferred embodiment, the one or more polar oils are selected from hydrocarbon-based oils of plant origin, synthetic esters of formula $R_1COOR_2$ in which $R_1$ represents the residue of a linear or branched fatty acid comprising from 1 to 40 carbon atoms and $R_2$ represents a hydrocarbon-based chain, especially branched, containing from 1 to 40 carbon atoms, with the proviso that $R_1+R_2$ is $\geq 10$, fatty alcohols which are liquid at room temperature and contain a branched and/or unsaturated carbon-based chain having from 12 to 26 carbon atoms, dialkyl carbonates, diesters of $C_2$-$C_{16}$ dicarboxylic acid and of $C_1$-$C_4$ monoalcohol, and combinations thereof.

In certain embodiments, the one or more polar oils are selected from triglycerides constituted of esters of glycerol and of linear or branched, saturated or unsaturated $C_4$ to $C_{24}$ fatty acids; esters of isopropyl alcohol and of $C_8$-$C_{18}$, preferably $C_{12}$-$C_{16}$, fatty acid; fatty alcohols which are liquid at room temperature and contain a branched and/or unsaturated carbon-based chain having from 16 to 22 carbon atoms, preferably from 18 to 20 carbon atoms; dialkyl carbonates, the two alkyl chains being identical, preferably dicaprylyl carbonate; diesters of $C_8$-$C_{12}$ dicarboxylic acid and of branched $C_3$-$C_4$ monoalcohol, preferably diisopropyl sebacate; and mixtures thereof.

The polar oil(s) within the context of the present invention may preferably be chosen from triglycerides of glycerol and of $C_6$-$C_{12}$ fatty acids, triglycerides of glycerol and of $C_{14}$-$C_{22}$ fatty acids, esters of isopropyl alcohol and of $C_8$-$C_{18}$ fatty acids, fatty alcohols which are liquid at room temperature and contain a branched and/or unsaturated carbon-based chain having from 18 to 20 carbon atoms, and mixtures thereof.

In certain embodiments, the one or more polar oils are selected from triglycerides of glycerol and of $C_{14}$-$C_{22}$ fatty acids comprising from 50% to 100% by weight of linear, branched, saturated or unsaturated $C_{18}$ fatty acids, including 0 to 5% by weight of saturated $C_{18}$ fatty acids such as stearic acid, from 50% to 98% by weight of monounsaturated fatty acids such as ricinoleic and/or oleic acids, and/or from 2% to 70% by weight of polyunsaturated $C_{18}$ fatty acids such as linoleic and/or linolenic acids, relative to the total weight of fatty acids contained within said triglycerides.

In certain embodiments, the one or more polar oils are selected from triglycerides of glycerol and of $C_6$-$C_{12}$ fatty acids comprise from 45% to 80% by weight of Ce fatty acids and from 20% to 45% by weight of $C_{10}$ fatty acids, relative to the total weight of fatty acids contained within said triglycerides.

In certain embodiments, the one or more polar oils are selected from fatty alcohols which are liquid at room temperature and contain a branched and/or unsaturated carbon-based chain having from 18 to 20 carbon atoms, triglycerides of glycerol and of $C_{14}$-$C_{22}$ fatty acids and mixtures thereof.

Preferably, the one or more polar oils are selected from vegetable oils. Nonlimiting but preferred vegetable oils include castor oil, corn oil, cottonseed oil, olive oil, peanut oil, rice bran oil, safflower oil, sunflower oil, sesame oil, soybean oil, hydrogenated soybean oil and hydrogenated vegetable oil; and triglyceride vegetable oils known as medium-chain triglycerides such as coconut oil or palm kernel oil-derived triglyceride vegetable oils. Furthermore, some special vegetable oils can be produced from a wide variety of plant grains and seeds. Nonlimiting examples of such oils include malt oil, pumpkin seed oil, linseed oil, grape seed oil, blackberry seed oil, annatto oil, peanut oil and various other oils.

The amount of the one or more polar oils in the fortifying composition, if present, will vary. Nonetheless, in certain embodiments, the fortifying composition includes about 0.1 to about 10 wt. %, based on a total weight of the fortifying composition. In further embodiments, the fortifying composition includes about 0.1 to about 8 wt. %, about 0.1 to about 5 wt. %, about 0.1 to about 3 wt. %, about 0.1 to about 2 wt. %, about 0.5 to about 10 wt. %, about 0.5 to about 8 wt. %, about 0.5 to about 5 wt. %, about 0.5 to about 3 wt. %, about 0.5 to about 2 wt. %, about 0.6 wt. %, about 0.7 wt. %, about 0.8 wt. %, about 0.9 wt. %, about 1 wt. %, about 1.1 wt. %, about 1.2 wt. %, or about 1.5 wt. % of the one or more polar oils, based on the total weight of the fortifying composition.

(g) Nonionic Surfactant or Emulsifier

The terms "nonionic surfactant" and "nonionic emulsifier" are used interchangeably in the instant disclosure and therefore can be referred to as "nonionic emulsifying surfactants." The nonionic surfactant or emulsifier may have an HLB (hydrophilic-lipophilic balance) ranging from 1 to 7.9 or greater than or equal to 8. "HLB" refers to the "hydrophilic-lipophilic balance" associated with nonionic surfactants or emulsifiers. In particular, "HLB" value relates to the ratio of hydrophilic groups and lipophilic groups in emulsifiers, and also relates to solubility of the emulsifiers. Lower HLB emulsifiers (such as those with HLB values ranging from 1 to 7.9) are more soluble in oils (lipophilic material) and are more appropriate for use in water-in-oil (W/O) emulsions. Higher HLB emulsifiers (such as those with HLB values higher than 8) are more soluble in water (hydrophilic material) and are more appropriate for oil-in-water (O/W) emulsions.

Nonlimiting examples of nonionic surfactants or emulsifiers include alkyl and polyalkyl esters of poly(ethylene oxide), alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, alkyl and polyalkyl glycosides or polyglycosides, in particular alkyl and polyalkyl glucosides or polyglucosides, alkyl and polyalkyl esters of sucrose, optionally polyoxyethylenated alkyl and polyalkyl esters of glycerol, and optionally polyoxyethylenated alkyl and polyalkyl ethers of glycerol, and mixtures thereof. Preferably, the nonionic surfactant(s) may be chosen from alkyl and polyalkyl esters of poly(ethylene oxide), alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, optionally polyoxyethylenated alkyl and polyalkyl esters of glycerol, and optionally polyoxyethylenated alkyl and polyalkyl ethers of glycerol, and mixtures thereof.

(1) Alkyl and polyalkyl esters of poly(ethylene oxide) that are preferably used are those containing at least one $C_8$-$C_{30}$ alkyl radical, with a number of ethylene oxide (EO) units ranging from 2 to 200. Mention may be made, for example, of (INCI name) PEG-20 stearate, PEG-40 stearate, PEG-100 stearate, PEG-20 laurate, PEG-8 laurate, PEG-40 laurate, PEG-150 distearate, PEG-7 cocoate, PEG-9 cocoate, PEG-8 oleate, PEG-10 oleate and PEG-40 hydrogenated castor oil.

(2) Alkyl and polyalkyl ethers of poly(ethylene oxide) that are preferably used are those containing at least one $C_8$-$C_{30}$ alkyl radical, with a number of ethylene oxide (EO) units ranging from 3 to 200. Mention may be made, for example, of laureth-3, laureth-4, laureth-7, laureth-23, ceteth-5, ceteth-7, ceteth-15, ceteth-23, oleth-5, oleth-7, oleth-10, oleth-12, oleth-20, oleth-50, phytosterol 30 EO, steareth-6, steareth-20, steareth-21, steareth-40, steareth-100, beheneth 100, ceteareth-7, ceteareth-10, ceteareth-15, ceteareth-25, pareth-3, pareth-23, $C_{12-15}$ pareth-3, C12-13 pareth-4, C12-13 pareth-23, trideceth-3, trideceth-4, trideceth-5, trideceth-6, trideceth-7 and trideceth-10, and mixtures thereof.

(3) Polyoxyethylenated alkyl and polyalkyl esters of sorbitan that are preferably used are those with a number of ethylene oxide (EO) units ranging from 0 to 100. Mention may be made, for example, of sorbitan laurate, sorbitan laurate 4 EO, sorbitan laurate 20 EO (polysorbate 20), sorbitan palmitate 20 EO (polysorbate 40), sorbitan stearate 20 EO (polysorbate 60), sorbitan oleate 20 EO (polysorbate 80) and sorbitan trioleate 20 EO (polysorbate 85).

(4) Polyoxyethylenated alkyl and polyalkyl ethers of sorbitan that are preferably used are those with a number of ethylene oxide (EO) units ranging from 0 to 100.

The fortifying compositions of the instant disclosure may include one or more alkanolamides. Non-limiting examples alkanolamides include fatty acid alkanolamides.

The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof);

$R_6$ is selected from —$CH_2OH$, —$CH_2CH_2OH$, —$CH_2CH_2CH_2OH$, —$CH_2(CHOH)_4CH_2OH$, -benzyl, and mixtures thereof;

$R_6$ is selected from —H, —$CH_3$, —$CH_2OH$, —$CH_2CH_3$, —$CH_2CH_2OH$, —$CH_2CH_2CH_2OH$, —$CH_2(CHOH)_4$ $CH_2OH$, -benzyl, and mixtures thereof.

In some instances, the one or more of the fatty acid alkanolamides include one or more acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleyl methylglucamide oleate, stearoyl methylglucamide stearate, sunfloweroyl methylglucamide, and tocopheryl succinate methylglucamide.

The fortifying compositions of the instant disclosure may include one or more alkyl polyglucosides. Non-limiting examples of alkyl polyglucosides include those having the following formula:

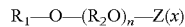

wherein $R_1$ is an alkyl group having 8-18 carbon atoms;
$R_2$ is an ethylene or propylene group;
Z is a saccharide group with 5 to 6 carbon atoms;
n is an integer from 0 to 10; and
x is an integer from 1 to 5.

Useful alkyl poly glucosides include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

The fortifying compositions of the instant disclosure may include one or more miscellaneous nonionic surfactants or emulsifiers. Nonlimiting examples include alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Such nonionic surfactants or emulsifiers may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant or emulsifier may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

The total amount of the one or more nonionic surfactants or emulsifiers in the fortifying composition, if present, will vary. Nonetheless, in certain embodiments, the fortifying composition includes about 0.01 to about 10 wt. % of the one or more nonionic surfactants or emulsifiers, based on the total weight of the fortifying composition. In further embodiments, the fortifying composition includes about 0.01 to about 8 wt. %, about 0.01 to about 5 wt. %, about 0.01 to about 3 wt. %, about 0.01 to about 1 wt. %, about 0.05 to about 10 wt. %, about 0.05 to about 8 wt. %, about 0.05 to about 5 wt. %, about 0.05 to about 3 wt. %, or about 0.05 to about 1 wt. % of the one or more nonionic surfactants or emulsifiers, based on a total weight of the composition.
(h) Miscellaneous Ingredients The fortifying composition optionally includes one or more miscellaneous ingredients. Miscellaneous ingredients are ingredients that are compatible with the fortifying composition and do not disrupt or materially affect the basic and novel properties of the fortifying composition. Nonlimiting examples of ingredients include preservatives, fragrances, pH adjusters, salts, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, etc. In various embodiments, the miscellaneous ingredients are chosen from preservatives, fragrances, pH adjusters, salts, chelating agents, buffers, composition colorants, and mixtures thereof. In the context of the instant disclosure, a "composition colorant" is a compound that colors the composition but does not have an appreciable coloring effect on hair. In other words, the composition colorant is included to provide a coloring to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair.

The total amount of the one or more miscellaneous ingredients in the fortifying composition, if present, will vary. Nonetheless, in various embodiments, the fortifying composition includes about 0.1 to about 15 wt. % of the one or more miscellaneous ingredients, based on the total weight of the compositions. In further embodiments, the fortifying composition includes about 0.1 to about 12 wt. %, about 0.1 to about 10 wt. %, about 0.1 to about 5 wt. %, about 0.5 to about 15 wt. %, about 0.5 to about 12 wt. %, about 0.5 to about 10 wt. %, about 0.5 to about 8 wt. %, about 0.5 to about 5 wt. %, about 1 to about 15 wt. %, about 1 to about 12 wt. %, about 1 to about 10 wt. %, about 1 to about 8 wt. %, about 1 to about 5 wt. %, about 2 to about 15 wt. %, about 2 to about 12 wt. %, about 2 to about 10 wt. %, about 2 to about 8 wt. %, or about 2 to about 5 wt. %, based on the total weight of the compositions.

pH

The pH of the fortifying composition will vary. Nonetheless, in certain embodiments, a pH less than 7 (an acidic pH) is desirable. For example, the pH can be from about 3 to about 6.5, about 3 to about 6, about 3 to about 5.5, about 3 to about 5, about 3 to about 4.5, about 3 to about 4, about 3.5 to about 6.5, about 3.5 to about 6, about 3.5 to about 5.5, about 3.5 to about 5, or about 3.5 to about 4.5, or about 3.5 to about 4.

Conditioning Composition (a) Cationic Surfactant

The term "cationic surfactant" as defined by the instant disclosure is a surfactant that may be positively charged when it is contained in the conditioning compositions according to the disclosure. The cationic surfactant may bear one or more positive permanent charges or may contain one or more functional groups that are cationizable in the conditioning composition according to the disclosure.

Mono-alkyl cationic surfactants useful herein are primary, secondary, and tertiary amines having one long alkyl or alkenyl group of from about 12 to about 30 carbon atoms, preferably from 16 to 24 carbon atoms, more preferably from 18 to 22 alkyl group. For example, mono-alkyl cationic surfactants include mono-alkyl trimonium halide compounds. Nonlimiting examples of mono-alkyl trimonium halide compounds include cetrimonium chloride, steartrimonium chloride, behentrimonium chloride, cocotrimonium chloride, cocamidopropyltrimonium chloride. Preferred are cetrimonium chloride, steartrimonium chloride and behentrimonium chloride.

In various embodiments, the conditioning compositions includes behentrimonium chloride, cetrimonium chloride, or a combination thereof.

Mono-alkyl cationic surfactants also include mono-alkyl amidoamines. Particularly useful are tertiary amidoamines having an alkyl group of from about 12 to about 22 carbon atoms, preferably from about 16 to about 22 carbon atoms. Exemplary tertiary amido amines include: stearamidopropyldimethylamine, stearamidopropyl-diethylamine, stearamidoethyldiethylamine, stearamidoethyldimethylamine, palmitamidopropyldimethylamine, palmitamidopropyldiethylamine, palmitamidoethyl-diethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethyl-stearamide, and a combination thereof.

Di-alkyl cationic surfactants includes those of formula (I) and salts thereof:

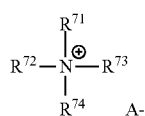

Formula (I)

wherein two of $R^{71}$, $R^{72}$, $R^{73}$, and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms, the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $A^-$ is an anion, for example, a halide, such as chloride or bromide, a C1-C4 alkyl sulfate such as methosulfate and ethosulfate, and mixtures thereof.

The aliphatic groups for Formula (I) can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Nonlimiting examples of di-alkyl cationic surfactants of Formula (I) include dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, dicetyldimonium chloride, dicetyldimonium bromide, and a combination thereof.

In a preferred embodiments, the one or more cationic surfactants are selected from cetrimonium chloride, stearimonium chloride, behentrimonium chloride, cetrimonium methosulfate, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof. Even more preferably, the cationic surfactants include cetrimonium chloride, behentrimonium chloride, cetrimonium methosulfate, behentrimonium methosulfate, of a combination thereof.

The total amount of the one or more cationic surfactants in the conditioning composition will vary. Nonetheless, in various embodiments, the conditioning compositions include about 1 to about 10 wt. % of the one or more cationic surfactants, based on a total weight of the composition. In further embodiments, the conditioning composition includes about 1 to about 8 wt. %, about 1 to about 6 wt. %, about 1 to about 5 wt. %, about 1 to about 4 wt. %, about 1 to about 3 wt. %, about 1.5 to about 10 wt. %, 1.5 to about 8 wt. %, about 1.5 to about 6 wt. %, about 1.5 to about 5 wt. %, about 1.5 to about 4 wt. %, about 1.5 to about 3 wt. %, about 2 to about 10 wt. %, about 2 to about 8 wt. %, about 2 to about 6 wt. %, about 2 to about 5 wt. %, about 2 to about 4 wt. %, about 2 to about 3 wt. %, or about 1 wt. %, 1.5 wt. %, 2 wt. %, about 2.5 wt. %, about 3 wt. %, about 3.5 wt. %, about 4 wt. %, about 4.5 wt. %, about 5 wt. %, about 6 wt. %, about 8 wt. %, or about 10 wt. % of the one or more cationic surfactants.

(b) Non-Silicone Fatty Compounds

The term "non-silicone fatty compound" is interchangeable with the term "non-silicone-based fatty compound" and means an organic compound without silicone that is insoluble in water at ordinary temperature (25° C.) and at atmospheric pressure (760 mmHg), i.e. which has a solubility of less than 5%, preferably less than 1% and even more preferentially less than 0.1%. They have in their structure a hydrocarbon-based chain containing at least 6 carbon atoms. Throughout the disclosure, any reference to "fatty compound" is considered a non-silicone fatty compound, even if the term "non-silicone" is not used.

More particularly, the one or more non-silicone-based fatty compounds may be selected from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, non-salified fatty acids, fatty acid and/or fatty alcohol esters other than triglycerides and plant waxes, non-silicone waxes and silicones, and mixtures thereof.

Fatty alcohols, fatty esters and fatty acids more particularly contain one or more linear or branched, saturated or unsaturated hydrocarbon-based groups comprising 6 to 30 carbon atoms, which are optionally substituted, in particular, with one or more (in particular 1 to 4) hydroxyl groups. If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the names Miglyol® 810, 812 and 818 by the company Dynamit Nobel, jojoba oil and shea butter oil.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050@ and PF 5060@ by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052@ by the company 3M.

The fatty alcohols that may be used in the conditioning composition may be saturated or unsaturated, linear or branched alcohols comprising from 6 to 30 carbon atoms and more particularly from 8 to 30 carbon atoms, among which mention may be made, for example, of cetyl alcohol, stearyl alcohol and the mixture thereof (cetylstearyl alcohol or cetearyl alcohol), octyldodecanol, 2-butyloctanol, 2-hexyldecanol, 2-undecylpentadecanol, oleyl alcohol or linoleyl alcohol.

The non-salified fatty acids that may be used in the conditioning composition may be saturated or unsaturated carboxylic acids comprising from 6 to 30 carbon atoms and in particular from 9 to 30 carbon atoms. They are more particularly chosen from myristic acid, palmitic acid, stearic acid, behenic acid, oleic acid, linoleic acid, linolenic acid and isostearic acid.

These acids are not salified. This means that they are introduced in the form of free acids and that the conditioning composition does not comprise any alkaline agent leading to their salification.

The esters of fatty acids and/or of fatty alcohols, advantageously different from the triglycerides mentioned above, which may be used in the conditioning compositioions are esters of saturated or unsaturated, linear or branched C1-C26 aliphatic mono- or polyacids and of saturated or unsaturated, linear or branched C1-C26 aliphatic mono- or polyalcohols, the total carbon number of the esters more particularly being greater than or equal to 10. Among the monoesters, mention may be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of C4-C22 dicarboxylic or tricarboxylic acids and of C1-C22 alcohols and esters of mono-, di- or tricarboxylic acids and of C2-C26 di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The esters according to this variant may also be chosen from monoesters, diesters, triesters, tetraesters and polyesters, and mixtures thereof. These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters. More particularly, use is made of monoesters and diesters and in particular mono- or di-oleate, -stearate, -behenate, -oleopalmitate, -linoleate, -linolenate or -oleostearate of sucrose, glucose or methylglucose.

The non-silicone wax(es) that may be used in the conditioning compositions are chosen especially from carnauba wax, candelilla wax, esparto grass wax, hydrocarbon waxes including paraffin wax, ozokerite and microcrystalline wax, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are especially marine waxes such as the product sold by the company Sophim under the reference M82, and polyethylene waxes or polyolefin waxes in general.

In a preferred embodiment, the one or more non-silicone fatty compounds are selected from oils, waxes, linear or branched alkanes, fatty esters, esters of fatty acids, esters of fatty alcohols, cetyl esters, triglycerides, or a mixture thereof. In certain embodiments, at least one of the non-silicone fatty compounds is a fatty alcohol. Preferably, the conditioning compositions includes: (i) one or more fatty alcohols; and (ii) one or more additional non-silicone fatty compounds, other than the one or more fatty alcohols.

(i) Fatty Alcohol

The term "fatty alcohol" means an alcohol comprising at least one hydroxyl group (OH), and typically comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In various embodiments, the conditioning compositions include at least one solid fatty alcohol. Solid fatty alcohols are fatty alcohols that are solid at ambient temperature and at atmospheric pressure (25° C., 780 mmHg), and are insoluble in water, i.e., they have a water solubility of less than 1% by weight, preferably less than 0.5% by weight, at 25° C., 1 atm. The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms. Nonlimiting examples include lauryl alcohol (1-dodecanol); myristyl alcohol (1-tetradecanol), cetyl alcohol (1-hexadecanol), stearyl alcohol (1-octadecanol), arachidyl alcohol (1-eicosanol), behenyl alcohol (1-docosanol), lignoceryl alcohol (1-tetracosanol), ceryl alcohol (1-hexacosanol), montanyl alcohol (1-octacosanol), myricylic alcohol (1-triacontanol), and combinations thereof. In a preferred embodiment, the conditioning compositions include at least one solid fatty alcohol selected from myristyl alcohol, cetyl alcohol, stearyl alcohol, behenyl alcohol and combinations thereof such as cetylstearyl or cetearyl alcohol.

In various embodiments, the conditioning compositions include at least one liquid fatty alcohol, in particular containing C10-C34 and preferably have branched carbon chains and/or have one or more, preferably 1 to 3 double bonds. They are preferably branched and/or unsaturated (C=C double bond) and contain from 12 to 40 carbon atoms. The liquid fatty alcohols may be represented by: R—OH, wherein R denotes a C12-C24 branched or straight alkyl group or an alkenyl group, R being optionally substituted by one or more hydroxy groups. In certain embodiments, the liquid fatty alcohols are selected from branched saturated alcohols. Preferably, R does not contain a hydroxyl group. Nonlimiting examples include oleyl alcohol, linoleyl alcohol, linolenyl alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and combinations thereof. In other embodiments, the conditioning compositions are free or essentially free from liquid fatty alcohols, including the liquid fatty alcohols referenced above.

In a preferred embodiment, the one or more fatty alcohols are linear (straight chain) saturated fatty alcohols having from 10 to 30 carbon atoms, preferably from 12 to 28 carbon atoms, more preferably from 14 to 24 carbon atoms. Non-limiting examples include decyl alcohol, undecyl alcohol, dodecyl alcohol, myristyl alcohol, cetyl alcohol, stearyl alcohol, cetearyl alcohol, behenyl alcohol, myricyl alcohol and a combination thereof.

The total amount of the one or more fatty alcohols in the conditioning composition will vary. Nonetheless, in various embodiments, the total amount of the one or more fatty alcohols is from about 1 to about 15 wt. %, preferably about 2 to about 15 wt. %, based on the total weight of the conditioning composition. In further embodiments, the conditioning composition includes about 1 to about 10 wt. %, about 1 to about 8 wt. %, about 2 to about 15 wt. %, about 2 to about 12 wt. %, about 2 to about 10 wt. %, about 2 to about 8 wt. %, about 3 to about 15 wt. %, about 3 to about 12 wt. %, about 3 to about 10 wt. %, about 3 to about 8 wt. %, or about 4 to about 8 wt. % of the one or more fatty alcohols, based on a total weight of the conditioning composition.

(ii) Additional Non-Silicone Fatty Compound

The additional non-silicone fatty compounds other than the one or more fatty alcohols include the one or more non-silicone fatty compounds mentioned above, under the heading "(ii)(b) Non-Silicone Fatty Compounds." The total amount of the one or more additional non-silicone fatty compounds (in addition to the one or more fatty alcohols), if present, will vary. Nonetheless, in certain embodiments, the conditioning composition includes about 0.1 to about 15 wt. % of the one or more additional non-silicone compounds. In further embodiments, the conditioning composition includes about 0.1 to about 12 wt. %, about 0.1 to about 10 wt. %, about 0.1 to about 8 wt. %, about 0.1 to about 5 wt. %, 1 to about 15 wt. %, about 1 to about 12 wt. %, about 1 to about 10 wt. %, about 1 to about 8 wt. %, about 1 to about 5 wt. %, about 2 to about 15 wt. %, about 2 to about 12 wt. %, about 2 to about 10 wt. %, about 2 to about 8 wt. %, about 2 to about 5 wt. %, or about 3 to about 6 wt. % of the one or more additional non-silicone fatty compounds, based on the total weight of the conditioning composition.

The total amount of the one or more non-silicone fatty compounds (fatty alcohols and/or the one or more additional non-silicone fatty compounds) in the conditioning compositions will vary. Nonetheless, in certain embodiments, the conditioning compositions include about 1 to about 20 wt. % of the one or more non-silicone fatty compounds, based on the total weight of the conditioning compositions. In further embodiments, the conditioning compositions include about 1 to about 15 wt. %, about 1 to about 12 wt. %, about 1 to about 10 wt. %, about 2 to about 20 wt. %, about 2 to about 15 wt. %, about 2 to about 12 wt. %, about 2 to about 10 wt. %, about 5 to about 20 wt. %, about 5 to about 15 wt. %, about 5 to about 12 wt. %, about 5 to about 10 wt. %, about 8 to about 20 wt. %, about 8 to about 15 wt. %, about 8 to about 12 wt. %, about 8 wt. %, 9 wt. %, 10 wt. %, 11 wt. %, 12 wt. %, 13 wt. %, or 14 wt. % of the one or more non-silicone fatty compounds, based on the total weight of the composition.

(c) Silicon Oil

Nonlimiting examples of silicone oils include dimethicone, dimethiconol, cyclomethicone, polysilicone-11, phenyl trimethicone, trimethylsilylamodimethicone, and stearoxytrimethylsilane. In a preferred embodiment, the one or more silicones are non-volatile silicone oils. Useful silicone oils include polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl (trimethylsiloxy)diphenylsiloxanes, diphenyl dimethicones, diphenyl(methyldiphenyl)trisiloxanes or 2-phenylethyl) trimethylsiloxysilicates. Other examples of silicone oils that may be mentioned include volatile linear or cyclic silicones, such as those with a viscosity 8 centistokes and/or containing from 2 to 7 silicon atoms. These silicones optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or combinations thereof. In various embodiments, the conditioning compositions include one or more silicone oils chosen from dimethicone, dimethiconol, cyclomethicone, polysilicone-11, phenyl trimethicone, and amodimethicone, aminopropyl dimethicone, and a combination thereof.

The total amount of the one or more silicone oils in the conditioning compositions, if present, will vary. Nonetheless, in certain embodiments, the conditioning compositions include about 0.1 to about 10 wt. % of the one or more silicone oils, based on the total weight of the conditioning composition. In further embodiments, the conditioning compositions include about 0.1 to about 8 wt. %, about 0.1 to about 5 wt. %, about 0.1 to about 3 wt. %, about 1 to about 10 wt. %, about 1 to about 8 wt. %, about 1 to about 5 wt.

%, about 1 to about 3 wt. %, about 2 to about 10 wt. %, about 2 to about 8 wt. %, about 2 to about 5 wt. %, or about 2 to about 3 wt. %, of the one or more silicone oils, based on the total weight of the conditioning composition.

Preferably, at least one of the one or more silicone oils is an amino-functionalized silicone. The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company. A particularly preferred amino-functionalized silicone is amodimethicone" A non-limiting example of amodimethicone products containing amino silicones having structure (D) re sold by Wacker under the name BELSIL ADM 652, BELSIL ADM 4000 E, or BELSIL ADM LOG 1. A product containing amino silicones having structure (E) is sold by Wacker under the name FLUID WR 1300. Additionally or alternative, the weight-average molecular weight (Mw) of the silicone ranges preferably from 2,000 to 200,000, even more particularly 5,000 to 100,000 and more particularly from 10,000 to 50,000.

In a preferred embodiment, the one or more amino-functionalized silicones are selected from amodimethicone, bis-hydroxy/methoxy amodimethicone, bis-cetearyl amodimethicone, bis(C13-15 alkoxy) PG amodimethicone, aminopropyl phenyl trimethicone, aminopropyl dimethicone, bis-amino PEG/PPG-41/3 aminoethyl PG-propyl dimethicone, or a mixture thereof. In a further preferred embodiments, the amino-functionalized silicone is amodimethicone.

The total amount of the one or more amino-functionalized silicones in the conditioning compositions, if present, will vary. Nonetheless, in certain embodiments, the conditioning compositions include about 0.1 to about 10 wt. % of the one or more amino-functionalized silicones, based on the total weight of the conditioning composition. In further embodiments, the conditioning compositions include about 0.1 to about 8 wt. %, about 0.1 to about 5 wt. %, about 0.1 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, about 2 to about 5 wt. %, or about 2 to about 3 wt. %, of the one or more amino-functionalized silicones, based on the total weight of the conditioning composition.

(d) Water

The total amount of water in the conditioning compositions will vary. Nonetheless, in certain embodiments, the conditioning compositions include about 50 to about 90 wt. % of water, based on the total weight of the conditioning composition. In further embodiments, the conditioning compositions include about 60 to about 90 wt. %, about 65 to about 90 wt. % about 70 to about 90 wt. %, about 50 to about 85 wt. %, about 60 to about 85 wt. %, about 65 to about 85 wt. %, about 70 to about 85 wt. %, about 75 to about 85 wt. %, about 78 wt. %, about 80 wt. %, about 82 wt. %, about 85 wt. % of water, based on a total weight of the conditioning composition.

(e) Thickening Agent

The conditioning composition may optionally include one or more thickening agents (also referred to as thickeners or viscosity modifying agents). Many thickening agents are water-soluble and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

Non-limiting examples of thickening agents include xanthan gum, guar gum, biosaccharide gum, cellulose, acacia Seneca gum, sclerotium gum, agarose, pectin, gellan gum, starch, and derivatives thereof. In some instances, the one or more thickening agents may include polymeric thickening agents, for example, those selected from polyvinvyl pyrrolidone, ammonium polyacryloyldimethyl taurate, ammonium acryloyldimethyltaurateNP copolymer, sodium polyacrylate, acrylates copolymers, polyacrylamide, carbomer, and acrylates/C10-30 alkyl acrylate crosspolymer.

(i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the "Carbopol® 900" series from B.F. Goodrich (e.g., "Carbopol® 954"). In addition, other suitable carboxylic acid polymeric agents include "Ultrez® 10" (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as "Carbopol® 1342," "Carbopol® 1382," "Pemulen TR-1", and "Pemulen TR-2" from B.F. Goodrich. In other words, examples of carboxylic acid polymer thickeners useful herein are those selected from carbomers, acrylates/C10-C30 alkyl acrylate crosspolymers, and combinations thereof. Further nonlimiting examples of thickening agents include crosslinked polyacrylate polymers, polyacrylamide polymers, polysaccharides, and gums, as set forth below.

(ii) Crosslinked Polyacrylate Polymers

The conditioning compositions of the present disclosure can optionally contain crosslinked polyacrylate polymers useful as thickeners or gelling agents including both cationic and nonionic polymers.

(iii) Polyacrylamide Polymers

The conditioning compositions of the present disclosure can optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the tradename "Sepigel 305" from Seppic Corporation.

Other polyacrylamide polymers useful herein include multi-block copolymers of acrylamides and substituted acrylamides with acrylic acids and substituted acrylic acids. Commercially available examples of these multi-block copolymers include "Hypan SR150H," "Hypan SS500V," "Hypan SS500W", and "Hypan SSSA100H" from Lipo Chemicals, Inc.

The conditioning compositions may also contain thickening and texturizing gels of the type as exemplified by the product range called "Lubrajel®" from United Guardian. These gels have moisturizing, viscosifying, and stabilizing properties.

(iv) Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and combinations thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename "Natrosol® CS Plus" from Aqualon Corporation.

Other useful polysaccharides include scleroglucans comprising a linear chain of (1-3) linked glucose units with a (1-6) linked glucose every three units, a commercially available example of which is "Clearogel™ CS11" from Michel Mercier Products Inc.

Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosaccharide gum, and combinations thereof.

Additional examples of water-soluble thickeners include water-soluble natural polymers, water-soluble synthetic polymers, clay minerals, and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, and hydroxypropyl starch).

The total amount of the one or more thickening agent, if present, will vary. Nonetheless, in certain embodiments, the conditioning composition include about 0.01 to about 8 wt. % of the one or more thickening agents. In further embodiments, the conditioning composition includes about 0.01 to about 5 wt. %, about 0.01 to about 3 wt. %, about 0.01 to about 2 wt. %, about 0.05 to about 8 wt. %, 0.05 to about 5 wt. %, about 0.05 to about 3 wt. %, about 0.05 to about 2 wt. %, about 0.1 to about 8 wt. %, about 0.1 to about 5 wt. %, about 0.1 to about 3 wt. %, about 0.1 to about 2 wt. %, about 0.5 to about 8 wt. %, about 0.5 to about 5 wt. %, about 0.5 to about 3 wt. %, or about 0.5 to about 2 wt. % of the one or more thickening agents, based on the total weight of the conditioning composition.

(f) Water-Soluble Solvent

The term "water soluble organic solvent" is interchangeable with the terms "water soluble solvent" and "water-miscible solvent" and means a compound that is liquid at 25° C. and at atmospheric pressure (760 mmHg), and it has a solubility of at least 50% in water under these conditions. In some cases, the water-soluble solvents has a solubility of at least 60%, 70%, 80%, or 90%. Non-limiting examples of water-soluble solvents include, for example, organic solvents selected from glycerin, alcohols (for example $C_{1-8}$, or $C_{1-4}$ alcohols), polyols (polyhydric alcohols), glycols, and a mixture thereof.

Nonlimiting examples of water-soluble organic solvents. Non-limiting examples of water-soluble organic solvents include, for example, organic solvents selected from glycerin, alcohols (for example, $C_{1-10}$, $C_{1-8}$, or $C_{1-4}$ alcohols), polyols (polyhydric alcohols), glycols, and a mixture thereof. Nonlimiting examples of monoalcohols and polyols include ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin.

Further non-limiting examples of water soluble organic solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In a preferred embodiment, the conditioning composition include one or more glycols selected from glycerin, propylene glycol, butylene glycol, pentylene glycol, hexylene glycol, caprylyl glycol, dipropylene glycol, and combinations thereof.

The total amount of the one or more water soluble solvents in the conditioning compositions, if present, will vary. Nonetheless, in various embodiments, the conditioning compositions include about 0.1 to about 20 wt. % of the one or more water soluble solvents, based on the total weight of the compositions. In further embodiments, the compositions include about 0.1 to about 15 wt. %, about 0.1 to about 10 wt. %, about 0.1 to about 8 wt. %, about 0.1 to about 5 wt. %, about 0.5 to about 20 wt. %, about 0.5 to about 15 wt. %, about 0.5 to about 10 wt. %, about 0.5 to about 8 wt. %, about 0.1 to about 5 wt. %, about 1 to about 20 wt. %, about 1 to about 15 wt. %, about 1 to about 10 wt. %, about 1 to about 8 wt. %, or about 1 to about 5 wt. % of the one or more water soluble solvents, based on the total weight of the conditioning compositions.

(g) Miscellaneous Ingredients

The conditioning compositions optionally include one or more miscellaneous ingredients. Miscellaneous ingredients are ingredients that are compatible with the conditioning compositions and do not disrupt or materially affect the basic and novel properties of the compositions. Nonlimiting examples of miscellaneous ingredients include preservatives, fragrances, pH adjusters, salts, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, etc. In various embodiments, the miscellaneous ingredients are chosen from preservatives, fragrances, pH adjusters, salts, chelating agents, buffers, composition colorants, and mixtures thereof. In the context of the instant disclosure, a "composition colorant" is a compound that colors the composition but does not have an appreciable coloring effect on hair. In other words, the composition colorant is included to provide a coloring to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair.

The total amount of the one or more miscellaneous ingredients in the conditioning compositions, if present, will vary. Nonetheless, in various embodiments, the conditioning compositions include about 0.1 to about 15 wt. % of the one or more miscellaneous ingredients, based on the total weight of the compositions. In further embodiments, the conditioning compositions include about 0.1 to about 12 wt. %, about 0.1 to about 10 wt. %, about 0.1 to about 5 wt. %, about 0.5 to about 15 wt. %, about 0.5 to about 12 wt. %, about 0.5 to about 10 wt. %, about 0.5 to about 8 wt. %, about 0.5 to about 5 wt. %, about 1 to about 15 wt. %, about 1 to about 12 wt. %, about 1 to about 10 wt. %, about 1 to about 8 wt. %, about 1 to about 5 wt. %, about 2 to about 15 wt. %, about 2 to about 12 wt. %, about 2 to about 10 wt. %, about 2 to about 8 wt. %, or about 2 to about 5 wt. %, based on the total weight of the conditioning compositions.

Methods

I. Pre-Treatment Routine

According to the so-called "pre-treatment routine," a fortifying composition is applied to hair to be oxidatively bleached or colored before oxidatively bleaching or coloring the hair. The fortifying composition is applied to the hair and allowed to remain on the hair for a first period of time. The fortifying composition can be applied to wet hair, damp hair, or dry hair. Furthermore, in certain embodiments, the hair is cleansed with a shampoo prior to application of the fortifying composition. After rinsing the shampoo from the hair, the hair will be wet or damp. The fortifying composition is then applied to the wet or damp hair and allowed to remain on the hair for a period of time. For instance, the fortifying composition can be applied immediately after rinsing the shampoo from the hair or within about 1 hour, within about 45 minutes, within about 30 minutes, within about 15 minutes, within about 10 minutes, within about 8 minutes, or within about 5 minutes from rinsing the shampoo from the hair.

The fortifying composition is applied to the hair and allowed to remain on the hair for a first period of time, which can vary. Nonetheless, in certain embodiments, the fortifying composition remains on the hair for a period of time of about 1 minute to about 1 hour. In further embodiments, the fortifying composition remains on the hair for a period of time of about 1 to about 45 minutes, about 1 to about 30 minutes, about 1 to about 20 minutes, about 1 to about 15 minutes, about 1 to about 10 minutes, about 2 minutes to about 1 hour, about 2 to about 45 minutes, about 2 to about 30 minutes, about 2 to about 20 minutes, about 2 to about 15 minutes, or about 2 to about 10 minutes. The fortifying composition and the hair can be massaged or otherwise manipulated to ensure the fortifying composition comes into contact with most of the hair.

Upon expiration of the first period of time, the fortifying composition is not rinsed from the hair. Without rinsing the fortifying composition from the hair, an oxidative bleaching or coloring composition is applied to the hair, i.e., the hair is subjected to a oxidative bleaching or coloring procedure. The bleaching or coloring composition remains on the hair as desired to ensure an acceptable degree of bleaching or coloring is achieved. For example, the oxidative bleaching or coloring composition may remain on the hair for about 5 minutes to about 2 hours, about 5 minutes to about 1.5 hours, about 5 minutes to about 1 hour, about 5 minutes to about 45 minutes, about 10 minutes to about 2 hours, about 10 minutes to about 1.5 hours, about 10 minutes to about 1 hour, or about 10 minutes to about 45 minutes. The oxidative bleaching or coloring composition remains on the hair for a time sufficient to achieve a desired degree of bleaching or coloring, which will vary depending on the content of oxidative bleaching or coloring composition, the degree of desired bleaching or coloring, the original color of the hair, the resiliency of the hair to oxidative bleaching and coloring, etc. When the oxidative bleaching or coloring procedure is completed, the hair is cleansed and rinsed. The oxidative bleaching or coloring composition may be initially rinsed from the hair to remove a large portion of the oxidative bleaching or coloring composition and the further cleansed using a shampoo, and the shampoo rinsed from the hair. In any event, after cleansing the hair with a shampoo and rinsing the shampoo from the hair, a conditioning composition is applied to the hair.

The conditioning composition is typically applied to the hair shortly after rinsing the shampoo from the hair and therefore the hair is wet or damp. For example, the conditioning composition can be applied to the hair within about 1 hour from rinsing the shampoo from the hair. In further embodiments, the conditioning composition is applied to the hair within 45 minutes, within 30 minutes, within 20 minutes, within 15 minutes, within 10 minutes, or within 5 minutes from rinsing the shampoo from the hair.

The conditioning composition is applied to the hair and allowed to remain on the hair for a second period of time, which will vary. Nonetheless, in certain embodiments, the conditioning composition remains on the hair for a period of time of about 1 minute to about 1 hour. In further embodiments, the conditioning composition remains on the hair for a period of time of about 1 to about 45 minutes, about 1 to about 30 minutes, about 1 to about 20 minutes, about 1 to about 15 minutes, about 1 to about 10 minutes, about 2 minutes to about 1 hour, about 2 to about 45 minutes, about 2 to about 30 minutes, about 2 to about 20 minutes, about 2 to about 15 minutes, or about 2 to about 10 minutes. The conditioning composition and the hair can be massaged or otherwise manipulated to ensure the conditioning composition comes into contact with most of the hair.

After expiration of the second period of time, the conditioning composition is rinsed from the hair. After rinsing the conditioning composition from the hair, the hair is conditioned and strengthened. The hair also exhibits improved curl retention, less frizz, and less propensity for frizzing. The method (routine) prevents, reduces, or remediates damage to the hair caused by the oxidative bleaching or coloring process.

In various embodiments, the methods described above (the pre-treatment routine) strengthens the hair, improves curl retention, prevents frizz, and/or remediates damage to the hair caused by oxidative bleaching or coloring of the hair to a greater extent than carrying out the methods (the pre-treatment routine) without pre-treating the hair with the fortifying composition prior to oxidatively bleaching or coloring the hair.

In various embodiments, the methods described above (the pre-treatment routine) strengthens the hair, improves curl retention, prevents frizz, and/or remediates damage to the hair caused by oxidative bleaching or coloring of the hair to a greater extent than carrying out the method (pre-treatment routine) with a comparative fortifying composition lacking the citric acid, a salt thereof, or a combination thereof of (i)(a) but is otherwise identical to the fortifying composition of the instant disclosure.

In various embodiments, the methods described above (the pre-treatment routine) improves curl retention, prevents frizz, and/or remediates damage to the hair caused by oxidative bleaching or coloring of the hair to a greater extent than carrying out the method (pre-treatment routine) with a comparative fortifying composition lacking the cyclodextrin, a salt thereof, or a combination thereof of (i)(b) but is otherwise identical to the fortifying composition of the instant disclosure.

In various embodiments, the methods described above (the pre-treatment routine) strengthens the hair, improves curl retention, prevents frizz, and/or remediates damage to the hair caused by oxidative bleaching or coloring of the hair to a greater extent than carrying out the methods with a comparative fortifying composition lacking the citric acid, a salt thereof, or a combination thereof of (i)(a) but is otherwise identical to the fortifying composition; and strengthens the hair, improves curl retention, prevents frizz, and/or remediates damage to the hair caused by oxidative bleaching or coloring of the hair to a greater extent than carrying out the method with a comparative fortifying composition lacking the cyclodextrin, a salt thereof, or a combination thereof of (i)(b) but is otherwise identical to the fortifying composition of the instant disclosure.

II. Post-Treatment Routine

According to the so-called "post-treatment routine," a fortifying composition is not applied to hair to be oxidatively bleached or colored before oxidatively bleaching or coloring the hair. Unlike the pre-treatment routine discussed above, in the post-treatment routine the fortifying compositions is not applied to the hair until after the hair has been oxidatively bleached or colored with an oxidative bleaching or coloring composition.

The oxidative bleaching or coloring composition can be applied to wet hair, damp hair, or dry hair. Nonetheless, in certain embodiments, the hair is cleansed with a shampoo prior to application of the oxidative bleaching or coloring composition. After rinsing the shampoo from the hair, the hair will be wet or damp. The oxidative bleaching or coloring composition is then applied to the wet or damp hair and allowed to remain on the hair for a period of time. For instance, the oxidative bleaching or coloring composition can be applied immediately after rinsing the shampoo from the hair or within about 1 hour, within about 45 minutes, within about 30 minutes, within about 15 minutes, within about 10 minutes, within about 8 minutes, or within about 5 minutes from rinsing the shampoo from the hair.

The bleaching or coloring composition remains on the hair as desired to ensure an acceptable degree of bleaching or coloring is achieved. For example, the oxidative bleaching or coloring composition may remain on the hair for about 5 minutes to about 2 hours, about 5 minutes to about 1.5 hours, about 5 minutes to about 1 hour, about 5 minutes to about 45 minutes, about 10 minutes to about 2 hours, about 10 minutes to about 1.5 hours, about 10 minutes to about 1 hour, or about 10 minutes to about 45 minutes. The oxidative bleaching or coloring composition remains on the hair for a time sufficient to achieve a desired degree of bleaching or coloring, which will vary depending on the content of oxidative bleaching or coloring composition, the degree of desired bleaching or coloring, the original color of the hair, the resiliency of the hair to oxidative bleaching and coloring, etc. When the oxidative bleaching or coloring procedure is completed, the hair is cleansed and rinsed. The oxidative bleaching or coloring composition may be initially rinsed from the hair to remove a large portion of the oxidative bleaching or coloring composition and further cleansed using a shampoo, and the shampoo rinsed from the hair. In any event, after cleansing the hair with a shampoo and rinsing the shampoo from the hair, a first application of the fortifying composition is applied to the hair.

The fortifying composition is first applied to the hair and allowed to remain on the hair for a first period of time, which can vary. Nonetheless, in certain embodiments, the first application of the fortifying composition remains on the hair for a period of time of about 1 minute to about 1 hour. In further embodiments, the first application of the fortifying composition remains on the hair for a period of time of about 1 to about 45 minutes, about 1 to about 30 minutes, about 1 to about 20 minutes, about 1 to about 15 minutes, about 1 to about 10 minutes, about 2 minutes to about 1 hour, about 2 to about 45 minutes, about 2 to about 30 minutes, about 2 to about 20 minutes, about 2 to about 15 minutes, or about 2 to about 10 minutes. The first application of the fortifying composition and the hair can be massaged or otherwise manipulated to ensure the first application of the fortifying composition comes into contact with most of the hair.

Upon expiration of the first period of time, the first application of the fortifying composition is not rinsed from the hair. Without rinsing the first application of the fortifying composition from the hair, the hair is cleansed with a shampoo. The shampoo can be applied directly to the hair upon which the fortifying composition has been applied, i.e., the shampoo can be layered onto the fortifying composition on the hair. Alternatively, the hair can be rinsed prior to application of the shampoo. Regardless, after the shampoo is rinsed from the hair, the hair is treated with a second application of the fortifying composition for a second period of time, which can vary. Nonetheless, in certain embodiments, the second application of the fortifying composition remains on the hair for a period of time of about 1 minute to about 1 hour. In further embodiments, the second application of the fortifying composition remains on the hair for a period of time of about 1 to about 45 minutes, about 1 to about 30 minutes, about 1 to about 20 minutes, about 1 to about 15 minutes, about 1 to about 10 minutes, about 2 minutes to about 1 hour, about 2 to about 45 minutes, about 2 to about 30 minutes, about 2 to about 20 minutes, about 2 to about 15 minutes, or about 2 to about 10 minutes. The second application of the fortifying composition and the hair can be massaged or otherwise manipulated to ensure the second application of the fortifying composition comes into contact with most of the hair.

Upon expiration of the second period of time, the second application of the fortifying composition is not rinsed from the hair. Without rinsing the second application of the fortifying composition from the hair, a conditioning composition is applied to the hair and allowed to remain on the hair for a third period of time, which will vary. Nonetheless, in certain embodiments, the conditioning composition remains on the hair for a period of time of about 1 minute to about 1 hour. In further embodiments, the conditioning composition remains on the hair for a period of time of about 1 to about 45 minutes, about 1 to about 30 minutes, about 1 to about 20 minutes, about 1 to about 15 minutes, about 1 to about 10 minutes, about 2 minutes to about 1 hour, about 2 to about 45 minutes, about 2 to about 30 minutes, about 2 to about 20 minutes, about 2 to about 15 minutes, or about 2 to about 10 minutes. The conditioning composition and the hair can be massaged or otherwise manipulated to ensure the conditioning composition comes into contact with most of the hair.

After expiration of the third period of time, the conditioning composition is rinsed from the hair. After rinsing the conditioning composition from the hair, the hair is conditioned and strengthened. The hair also exhibits improved curl retention, less frizz, and less propensity for frizzing. The method (routine) prevents, reduces, or remediates damage to the hair caused by the oxidative bleaching or coloring process.

In various embodiments, the methods described above (the post-treatment routine) strengthens the hair, improves curl retention, prevents frizz, and/or remediates damage to the hair caused by oxidative bleaching or coloring of the hair to a greater extent than carrying out the methods (the post-treatment routine) without pre-treating the hair with the fortifying composition prior to oxidatively bleaching or coloring the hair.

In various embodiments, the methods described above (the post-treatment routine) strengthens the hair, improves curl retention, prevents frizz, and/or remediates damage to the hair caused by oxidative bleaching or coloring of the hair to a greater extent than carrying out the method (post-treatment routine) with a comparative fortifying composition lacking the citric acid, a salt thereof, or a combination thereof of (i)(a) but is otherwise identical to the fortifying composition of the instant disclosure.

In various embodiments, the methods described above (the post-treatment routine) improves curl retention, prevents frizz, and/or remediates damage to the hair caused by oxidative bleaching or coloring of the hair to a greater extent than carrying out the method (post-treatment routine) with a comparative fortifying composition lacking the cyclodextrin, a salt thereof, or a combination thereof of (i)(b) but is otherwise identical to the fortifying composition of the instant disclosure.

In various embodiments, the methods described above (the post-treatment routine) strengthens the hair, improves curl retention, prevents frizz, and/or remediates damage to the hair caused by oxidative bleaching or coloring of the hair to a greater extent than carrying out the methods with a comparative fortifying composition lacking the citric acid, a salt thereof, or a combination thereof of (i)(a) but is otherwise identical to the fortifying composition; and strengthens the hair, improves curl retention, prevents frizz, and/or remediates damage to the hair caused by oxidative bleaching or coloring of the hair to a greater extent than carrying out the method with a comparative fortifying composition lacking the cyclodextrin, a salt thereof, or a combination thereof of (i)(b) but is otherwise identical to the fortifying composition of the instant disclosure.

EMBODIMENTS

In various embodiments, the methods according to the instant disclosure comprise, consist essentially of, or consist of:
(i) applying a fortifying composition to hair to be oxidatively bleached or colored and allowing the fortifying composition to remain on the hair for a first period of time of about 1 minute to about 1 hour, preferably about 2 minutes to about 30 minutes, more preferably about 2 minutes to about 10 minutes, the fortifying composition comprising, consisting essentially of, or consisting of:

(a) about 1 to about 10 wt. %, preferably about 1.5 to about 6 wt. %, more preferably about 2 to about 5 wt. % of citric acid, a salt thereof, or a combination thereof;

(b) about 0.5 to about 10 wt. %, preferably about 1 to about 6 wt. %, more preferably about 1 to about 4 wt. % of cyclodextrin, a derivative thereof, or a combination therefore, wherein the cyclodextrin or derivative thereof is preferably a cyclodextrin or derivative of α-cyclodextrin, ß-cyclodextrin, γ-cyclodextrin, methyl derivatives of α-cyclodextrin, ß-cyclodextrin, or γ-cyclodextrin, hydroxypropyl derivatives of α-cyclodextrin, ß-cyclodextrin, or γ-cyclodextrin, or mixtures thereof, more preferably ß-cyclodextrin;

wherein a combined total amount of (a) and (b) is about 2 to about 15 wt. %, preferably about 2 to about 8 wt. %, more preferably about 3 to about 6 wt. %;

(c) about 0.1 to about 10 wt. %, preferably about 0.1 to about 6 wt. %, more preferably about 0.5 to about 5 wt. % of one or more polyols having from 2 to 10 carbon atoms, preferably selected from ethylene glycol, propylene glycol, butylene glycol, hexylene glycol, pentylene glycol, diethylene glycol, dipropylene glycol, 1,3 propanediol, glycerin, or combinations thereof, wherein more preferably at least one of the one or more polyols having from 2 to 10 carbon atoms is glycerin;

(d) about 60 to about 96 wt. %, preferably about 75 to about 95 wt. %, more preferably about 85 to about 96 wt. % of water;

(e) optionally, about 0.05 to about 5 wt. %, preferably about 0.1 to about 4 wt. %, more preferably about 0.5 to about 4 wt. % of one or more cationic polysaccharides, preferably wherein the one or more cationic polysaccharides are selected from cationic guars, cationic celluloses (also referred to as cationic cellulose polymers), cationic starches, cationic gums, cationic callose, cationic xylan, cationic mannan, cationic galactomannan, or a combination thereof, wherein more preferably, the one or more cationic polysaccharides are selected from cationic guars (also referred to as cationic guar derivatives), preferably wherein the cationic guars are selected from cationic hydroxyethyl guar, cationic hydroxypropyl guar, cationic hydroxybutyl guar, and cationic carboxylalkyl guars including cationic carboxymethyl guar, cationic alkylcarboxy guars such as cationic carboxylpropyl guar, cationic carboxybutyl guar, cationic carboxymethylhydroxypropyl guar, especially, guar hydroxypropyltrimonium chloride, hydroxypropyl guar hydroxypropyltrimonium chloride, or a combination thereof;

(f) optionally, about 0.1 to about 10 wt. %, preferably about 0.1 to about 5 wt. %, more preferably about 0.5 to about 4 wt. % of one or more polar oils, wherein preferably, the one or more polar oils are selected from nonvolatile polar oils, more preferably wherein the one or more polar oils are selected from vegetable oils, for example, castor oil, corn oil, cottonseed oil, olive oil, peanut oil, rice bran oil, safflower oil, sunflower oil, sesame oil, soybean oil, hydrogenated soybean oil and hydrogenated vegetable oil; and triglyceride vegetable oils known as medium-chain triglycerides such as coconut oil or palm kernel oil-derived triglyceride vegetable oils. Furthermore, some special vegetable oils can be produced from a wide variety of plant grains and seeds. Nonlimiting examples of such oils include malt oil, pumpkin seed oil, linseed oil, grape seed oil, blackberry seed oil, annatto oil, peanut oil, or a combination thereof;

(g) optionally, about 0.01 to about 10 wt. %, more preferably about 0.05 to about 5 wt. %, more preferably about 0.05 to about 3 wt. % of one or more nonionic emulsifiers, wherein preferably, at least one of the one or more nonionic surfactants is polyoxyalkylenated or polyglycerolated nonionic surfactants, more preferably, wherein the one or more nonionic surfactant is selected from alkyl and polyalkyl esters of poly(ethylene oxide) containing at least one $C_8$-$C_{30}$ alkyl radical, with a number of ethylene oxide (EO) units ranging from 2 to 200, for example, PEG-20 stearate, PEG-40 stearate, PEG-100 stearate, PEG-20 laurate, PEG-8 laurate, PEG-40 laurate, PEG-150 distearate, PEG-7 cocoate, PEG-9 cococate, PEG-8 oleate, PEG-10 oleate and PEG-40 hydrogenated castor oil; and (h) optionally, optionally, about 0.01 to about 10 wt. %, preferably about 0.1 to about 8 wt. %, more preferably about 1 to about 5 wt. % of one or more miscellaneous ingredients, preferably selected from preservatives, fragrances, pH adjusters, salts, chelating agents, buffers, antioxidants, flavonoids, vitamins, amino acids, botanical extracts, UV filtering agents, peptides, proteins, protein hydrolysates, and/or isolates, fillers (e.g., organic and/or inorganic fillers such as talc, calcium carbonate, silica, particular materials, etc.), emollients, composition colorants, or a mixture thereof;

wherein all weight percentages of (i) are based on a total weight of the fortifying composition;

(ii) after the first period of time, without rinsing the fortifying composition from the hair, applying an oxidative bleaching or coloring composition to the hair and oxidatively bleaching or coloring the hair;

(iii) after oxidatively bleaching or coloring the hair, removing the oxidative bleaching or coloring composition from the hair by washing the hair with a shampoo;

(iv) within about 1 hour, preferably within 30 minutes, more preferably within 10 minutes of after rinsing the shampoo from the hair, applying a conditioning composition to the hair and allowing the conditioning composition to remain on the hair for a second period of time of about 1 minute to about 1 hour, preferably about 2 minutes to about 30 minutes, more preferably about 2 minutes to about 10 minutes, the conditioning composition comprising, consisting essentially of, or consisting of;

(a) about 0.5 to about 10 wt. %, preferably about 1 to about 6 wt. %, more preferably about 2 to about 5 wt. %, of one or more cationic surfactants, preferably wherein the one or more cationic surfactants are selected from cetrimonium chloride, stearimonium chloride, behentrimonium chloride, cetrimonium methosulfate, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and a mixture thereof, more preferably wherein the cationic surfactants are selected from cetrimonium chloride, behentrimonium chloride, cetrimonium methosulfate, behentrimonium methosulfate, of a combination thereof;

(b) about 1 to about 20 wt. %, preferably about 2 to about 20 wt. %, more preferably about 3 to about 15 wt. % of one or more non-silicone fatty compounds; wherein preferably the one or more non-silicone fatty compounds include:
  (i) about 1 to about 15 wt. %, preferably about 2 to about 12 wt. %, more preferably about 3 to about 10 wt. % of one or more fatty alcohols, preferably wherein the one or more fatty alchols are selected from those having from 14 to 24 carbon atoms, more preferably wherein the one or more fatty alcohols are selected from decyl alcohol, undecyl alcohol, dodecyl alcohol, myristyl alcohol, cetyl alcohol, stearyl alcohol, cetearyl alcohol, behenyl alcohol, myricyl alcohol and a combination thereof; and
  (ii) about 1 to about 15 wt. %, preferably about 2 to about 12 wt. %, more preferably about 2 to about 8 wt. % of about one or more additional non-silicone compounds, preferably wherein the one or more additional non-silicone compounds are selected from non-silicone oils, waxes, linear or branched alkanes, fatty ester oils, esters of fatty acids, esters of fatty alcohols, cetyl esters, triglycerides, or a mixture thereof;

(c) about 0.1 to about 10 wt. %, preferably about 0.5 to about 6 wt. %, more preferably about 1 to about 5 wt. % of one or more silicone oils, wherein preferably, at least one of the one or more silicone oils is an amino-functionalized silicone, more preferably, wherein the at least one amino-functionalized silicone is selected from amodimethicone, bis-hydroxy/methoxy amodimethicone, bis-cetearyl amodimethicone, bis($C_{13-15}$ alkoxy) PG amodimethicone, aminopropyl phenyl trimethicone, aminopropyl dimethicone, bis-amino PEG/PPG-41/3 aminoethyl PG-propyl dimethicone, or a mixture;

(d) 50 to about 90 wt. % of water, preferably about 65 to about 90 wt. % water, more preferably about 75 to about 85 wt. % of water;

(e) optionally, about 0.01 to about 8 wt. %, preferably about 0.05 to about 5 wt. %, more preferably about 0.1 to about 5 wt. % of one or more thickening agents, preferably wherein the one or more thickening agents are water soluble thickening polymers, preferably selected from polysaccharide thickening agents, carboxylic acid polymers, crosslinked polyacrylate polymers, polyacrylamide polymers, gums, or a combination thereof, more preferably wherein the one or more thickening agents is selected from polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, and hydroxypropyl starch), or a combination thereof;

(f) optionally, about 0.1 to about 15 wt. %, preferably about 0.5 to about 10 wt. %, more preferably about 0.5 to about 5 wt. % of one or more water soluble solvents, preferably wherein the one or more water soluble solvents are selected from glycerin, $C_2$-$C_6$ mono-alcohols, polyols having from, glycols, or a mixture thereof, more preferably, selected from ethylene glycol, propylene glycol, butylene glycol, hexylene glycol, pentylene glycol, diethylene glycol, dipropylene glycol, 1,3 propanediol, glycerin, or a combination thereof; and (g) optionally, optionally, about 0.01 to about 10 wt. %, preferably about 0.1 to about 8 wt. %, more preferably about 1 to about 5 wt. % of one or more miscellaneous ingredients, preferably selected from preservatives, fragrances, pH adjusters, salts, chelating agents, buffers, antioxidants, flavonoids, vitamins, amino acids, botanical extracts, UV filtering agents, peptides, proteins, protein hydrolysates, and/or isolates, fillers (e.g., organic and/or inorganic fillers such as talc, calcium carbonate, silica, particular materials, etc.), emollients, composition colorants, or a mixture thereof;
  wherein all weight percentages of (iv) are based on a total weight of the conditioning composition; and (v) rinsing the conditioning composition from the hair after the second period of time.

In an embodiment, the methods described above (the pre-treatment routine) strengthens the hair, improves curl retention, prevents frizz, and/or remediates damage to the hair caused by oxidative bleaching or coloring of the hair to a greater extent than carrying out the methods (the pre-treatment routine) without pre-treating the hair with the fortifying composition prior to oxidatively bleaching or coloring the hair.

In another embodiment, the methods described above (the pre-treatment routine) strengthens the hair, improves curl retention, prevents frizz, and/or remediates damage to the hair caused by oxidative bleaching or coloring of the hair to a greater extent than carrying out the method (pre-treatment routine) with a comparative fortifying composition lacking the citric acid, a salt thereof, or a combination thereof of (i)(a) but is otherwise identical to the fortifying composition of the instant disclosure.

In another embodiment, the methods described above (the pre-treatment routine) improves curl retention, prevents frizz, and/or remediates damage to the hair caused by oxidative bleaching or coloring of the hair to a greater extent than carrying out the method (pre-treatment routine) with a comparative fortifying composition lacking the cyclodextrin, a salt thereof, or a combination thereof of (i)(b) but is otherwise identical to the fortifying composition of the instant disclosure.

In yet another embodiment, the methods described above (the pre-treatment routine) strengthens the hair, improves curl retention, prevents frizz, and/or remediates damage to the hair caused by oxidative bleaching or coloring of the hair to a greater extent than carrying out the methods with a comparative fortifying composition lacking the citric acid, a salt thereof, or a combination thereof of (i)(a) but is otherwise identical to the fortifying composition; and strengthens the hair, improves curl retention, prevents frizz, and/or remediates damage to the hair caused by oxidative bleaching or coloring of the hair to a greater extent than carrying out the method with a comparative fortifying composition lacking the cyclodextrin, a salt thereof, or a combination thereof of (i)(b) but is otherwise identical to the fortifying composition of the instant disclosure.

In further embodiments, the methods according to the instant disclosure comprise or consist of:
(i) applying an oxidative bleaching or coloring composition to the hair and oxidatively bleaching or coloring the hair, followed by cleansing the oxidative bleaching or coloring composition from the hair with a shampoo;
(ii) with about 1 hour, preferably within about 30 minutes, more preferably within about 10 from rinsing the shampoo from the hair, applying a first application of a fortifying composition to the hair, and allowing the first application of the fortifying composition to remain on the hair for a first period of time of about 1 minute to about 1 hour, preferably about 1 minute to about 30 minutes, more preferably from about 2 minutes to about 10 minutes, the fortifying composition comprising, consisting essentially of, or consisting of:
   (a) about 1 to about 10 wt. %, preferably about 1.5 to about 6 wt. %, more preferably about 2 to about 5 wt. % of citric acid, a salt thereof, or a combination thereof;
   (b) about 0.5 to about 10 wt. %, preferably about 1 to about 6 wt. %, more preferably about 1 to about 4 wt. % of cyclodextrin, a derivative thereof, or a combination therefore, wherein the cyclodextrin or derivative thereof is preferably a cyclodextrin or derivative of α-cyclodextrin, ß-cyclodextrin, γ-cyclodextrin, methyl derivatives of α-cyclodextrin, ß-cyclodextrin, or γ-cyclodextrin, hydroxypropyl derivatives of α-cyclodextrin, ß-cyclodextrin, or γ-cyclodextrin, or mixtures thereof, more preferably ß-cyclodextrin;
      wherein a combined total amount of (a) and (b) is about 2 to about 15 wt. %, preferably about 2 to about 8 wt. %, more preferably about 3 to about 6 wt. %;
   (c) about 0.1 to about 10 wt. %, preferably about 0.1 to about 6 wt. %, more preferably about 0.5 to about 5 wt. % of one or more polyols having from 2 to 10 carbon atoms, preferably selected from ethylene glycol, propylene glycol, butylene glycol, hexylene glycol, pentylene glycol, diethylene glycol, dipropylene glycol, 1,3 propanediol, glycerin, or combinations thereof, wherein more preferably at least one of the one or more polyols having from 2 to 10 carbon atoms is glycerin;
   (d) about 60 to about 96 wt. %, preferably about 75 to about 95 wt. %, more preferably about 85 to about 96 wt. % of water;
   (e) optionally, about 0.05 to about 5 wt. %, preferably about 0.1 to about 4 wt. %, more preferably about 0.5 to about 4 wt. % of one or more cationic polysaccharides, preferably wherein the one or more cationic polysaccharides are selected from cationic guars, cationic celluloses (also referred to as cationic cellulose polymers), cationic starches, cationic gums, cationic callose, cationic xylan, cationic mannan, cationic galactomannan, or a combination thereof, wherein more preferably, the one or more cationic polysaccharides are selected from cationic guars (also referred to as cationic guar derivatives), preferably wherein the cationic guars are selected from cationic hydroxyethyl guar, cationic hydroxypropyl guar, cationic hydroxybutyl guar, and cationic carboxylalkyl guars including cationic carboxymethyl guar, cationic alkylcarboxy guars such as cationic carboxylpropyl guar, cationic carboxybutyl guar, cationic carboxymethylhydroxypropyl guar, especially, guar hydroxypropyltrimonium chloride, hydroxypropyl guar hydroxypropyltrimonium chloride, or a combination thereof;
   (f) optionally, about 0.1 to about 10 wt. %, preferably about 0.1 to about 5 wt. %, more preferably about 0.5 to about 4 wt. % of one or more polar oils, wherein preferably, the one or more polar oils are selected from nonvolatile polar oils, more preferably wherein the one or more polar oils are selected from vegetable oils, for example, castor oil, corn oil, cottonseed oil, olive oil, peanut oil, rice bran oil, safflower oil, sunflower oil, sesame oil, soybean oil, hydrogenated soybean oil and hydrogenated vegetable oil; and triglyceride vegetable oils known as medium-chain triglycerides such as coconut oil or palm kernel oil-derived triglyceride vegetable oils. Furthermore, some special vegetable oils can be produced from a wide variety of plant grains and seeds. Nonlimiting examples of such oils include malt oil, pumpkin seed oil, linseed oil, grape seed oil, blackberry seed oil, annatto oil, peanut oil, or a combination thereof;
   (g) optionally, about 0.01 to about 10 wt. %, more preferably about 0.05 to about 5 wt. %, more preferably about 0.05 to about 3 wt. % of one or more nonionic emulsifiers, wherein preferably, at least one of the one or more nonionic surfactants is polyoxyalkylenated or polyglycerolated nonionic surfactants, more preferably, wherein the one or more nonionic surfactant is selected from alkyl and polyalkyl esters of poly(ethylene oxide) containing at least one $C_8$-$C_{30}$ alkyl radical, with a number of ethylene oxide (EO) units ranging from 2 to 200, for example, PEG-20 stearate, PEG-40 stearate, PEG-100 stearate, PEG-20 laurate, PEG-8 laurate, PEG-40 laurate, PEG-150 distearate, PEG-7 cocoate, PEG-9 cococate, PEG-8 oleate, PEG-10 oleate and PEG-40 hydrogenated castor oil; and
   (h) optionally, optionally, about 0.01 to about 10 wt. %, preferably about 0.1 to about 8 wt. %, more preferably about 1 to about 5 wt. % of one or more miscellaneous ingredients, preferably selected from preservatives, fragrances, pH adjusters, salts, chelating agents, buffers, antioxidants, flavonoids, vitamins, amino acids, botanical extracts, UV filtering agents, peptides, proteins, protein hydrolysates, and/or isolates, fillers (e.g., organic and/or inorganic fillers such as talc, calcium carbonate, silica, particular materials, etc.), emollients, composition colorants, or a mixture thereof;
      wherein all weight percentages of (ii) are based on a total weight of the fortifying composition;
(iii) upon expiration of the first period of time, cleansing the hair with a shampoo;
(iv) with about 1 hour, preferably 30 minutes, more preferably 10 minutes from rinsing the shampoo from the hair, applying a second application of the fortifying composition to the hair and allowing the second application of the fortifying composition to remain on the hair for a second period of time of about 1 minute to about 1 hour, preferably about 1 minute to about 30 minutes, more preferably about 2 minutes to about 10 minutes;

(v) upon expiration of the second period of time, without rinsing the second application of the fortifying composition from the hair, applying a conditioning composition to the hair and allowing the conditioning composition to remain on the hair for a third period of time of about 1 minute to about 1 hour, about 1 minute to about 30 minutes, about 2 minutes to about 10 minutes, the conditioning composition comprising, consisting essentially of or consisting of:

(a) about 0.5 to about 10 wt. %, preferably about 1 to about 6 wt. %, more preferably about 2 to about 5 wt. %, of one or more cationic surfactants, preferably wherein the one or more cationic surfactants are selected from cetrimonium chloride, stearimonium chloride, behentrimonium chloride, cetrimonium methosulfate, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and a mixture thereof, more preferably wherein the cationic surfactants are selected from cetrimonium chloride, behentrimonium chloride, cetrimonium methosulfate, behentrimonium methosulfate, of a combination thereof, (b) about 1 to about 20 wt. %, preferably about 2 to about 20 wt. %, more preferably about 3 to about 15 wt. % of one or more non-silicone fatty compounds; wherein preferably the one or more non-silicone fatty compounds include:

(i) about 1 to about 15 wt. %, preferably about 2 to about 12 wt. %, more preferably about 3 to about 10 wt. % of one or more fatty alcohols, preferably wherein the one or more fatty alchols are selected from those having from 14 to 24 carbon atoms, more preferably wherein the one or more fatty alcohols are selected from decyl alcohol, undecyl alcohol, dodecyl alcohol, myristyl alcohol, cetyl alcohol, stearyl alcohol, cetearyl alcohol, behenyl alcohol, myricyl alcohol and a combination thereof; and (ii) about 1 to about 15 wt. %, preferably about 2 to about 12 wt. %, more preferably about 2 to about 8 wt. % of about one or more additional non-silicone compounds, preferably wherein the one or more additional non-silicone compounds are selected from non-silicone oils, waxes, linear or branched alkanes, fatty ester oils, esters of fatty acids, esters of fatty alcohols, cetyl esters, triglycerides, or a mixture thereof;

(c) about 0.1 to about 10 wt. %, preferably about 0.5 to about 6 wt. %, more preferably about 1 to about 5 wt. % of one or more silicone oils, wherein preferably, at least one of the one or more silicone oils is an amino-functionalized silicone, more preferably, wherein the at least one amino-functionalized silicone is selected from amodimethicone, bis-hydroxy/methoxy amodimethicone, bis-cetearyl amodimethicone, bis(C13-15 alkoxy) PG amodimethicone, aminopropyl phenyl trimethicone, aminopropyl dimethicone, bis-amino PEG/PPG-41/3 aminoethyl PG-propyl dimethicone, or a mixture;

(d) 50 to about 90 wt. % of water, preferably about 65 to about 90 wt. % water, more preferably about 75 to about 85 wt. % of water;

(e) optionally, about 0.01 to about 8 wt. %, preferably about 0.05 to about 5 wt. %, more preferably about 0.1 to about 5 wt. % of one or more thickening agents, preferably wherein the one or more thickening agents are water soluble thickening polymers, preferably selected from polysaccharide thickening agents, carboxylic acid polymers, crosslinked polyacrylate polymers, polyacrylamide polymers, gums, or a combination thereof, more preferably wherein the one or more thickening agents is selected from polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, and hydroxypropyl starch), or a combination thereof;

(f) optionally, about 0.1 to about 15 wt. %, preferably about 0.5 to about 10 wt. %, more preferably about 0.5 to about 5 wt. % of one or more water soluble solvents, preferably wherein the one or more water soluble solvents are selected from glycerin, $C_2$-$C_6$ mono-alcohols, polyols having from, glycols, or a mixture thereof, more preferably, selected from ethylene glycol, propylene glycol, butylene glycol, hexylene glycol, pentylene glycol, diethylene glycol, dipropylene glycol, 1,3 propanediol, glycerin, or a combination thereof; and (g) optionally, optionally, about 0.01 to about 10 wt. %, preferably about 0.1 to about 8 wt. %, more preferably about 1 to about 5 wt. % of one or more miscellaneous ingredients, preferably selected from preservatives, fragrances, pH adjusters, salts, chelating agents, buffers, antioxidants, flavonoids, vitamins, amino acids, botanical extracts, UV filtering agents, peptides, proteins, protein hydrolysates, and/or isolates, fillers (e.g., organic and/or inorganic fillers such as talc, calcium carbonate, silica, particular materials, etc.), emollients, composition colorants, or a mixture thereof;

wherein all weight percentages of (v) are based on a total weight of the conditioning composition; and (vi) upon expiration of the third period of time, rinsing the fortifying composition and the conditioning composition from the hair.

In an embodiment, the methods described above (the post-treatment routine) strengthens the hair, improves curl retention, prevents frizz, and/or remediates damage to the hair caused by oxidative bleaching or coloring of the hair to a greater extent than carrying out the methods (the post-treatment routine) without pre-treating the hair with the fortifying composition prior to oxidatively bleaching or coloring the hair.

In another embodiment, the methods described above (the post-treatment routine) strengthens the hair, improves curl retention, prevents frizz, and/or remediates damage to the hair caused by oxidative bleaching or coloring of the hair to a greater extent than carrying out the method (post-treatment routine) with a comparative fortifying composition lacking the citric acid, a salt thereof, or a combination thereof of (i)(a) but is otherwise identical to the fortifying composition of the instant disclosure.

In another embodiment, the methods described above (the post-treatment routine) improves curl retention, prevents frizz, and/or remediates damage to the hair caused by oxidative bleaching or coloring of the hair to a greater extent than carrying out the method (post-treatment routine) with a comparative fortifying composition lacking the cyclodextrin, a salt thereof, or a combination thereof of (i)(b) but is otherwise identical to the fortifying composition of the instant disclosure.

In in yet another embodiment, the methods described above (the post-treatment routine) strengthens the hair, improves curl retention, prevents frizz, and/or remediates damage to the hair caused by oxidative bleaching or coloring of the hair to a greater extent than carrying out the methods with a comparative fortifying composition lacking the citric acid, a salt thereof, or a combination thereof of (i)(a) but is otherwise identical to the fortifying composition; and strengthens the hair, improves curl retention, prevents frizz, and/or remediates damage to the hair caused by oxidative bleaching or coloring of the hair to a greater extent than carrying out the method with a comparative fortifying composition lacking the cyclodextrin, a salt thereof, or a combination thereof of (i)(b) but is otherwise identical to the fortifying composition of the instant disclosure.

Implementation of the present disclosure is provided by way of the following examples. The examples serve to illustrate the technology without being limiting in nature.

Example 1
(Fortifying Compositions)

| | | | A | B | C |
|---|---|---|---|---|---|
| (a) | Citric Acid | CITRIC ACID | 2.5 | 2.5 | 2.5 |
| (b) | Cyclodextrin | CYCLODEXTRIN | 1.5 | 1.5 | 1.5 |
| Total (a) + (b) | | | 4 | 4 | 4 |
| Weight Ratio of (a):(b) | | | 1.7:1 | 1.7:1 | 1.7:1 |
| Molar Ratio of (a):(b) | | | 10:1 | 10:1 | 10:1 |
| (c) | Polyol | GLYCERIN | | 1 | 1 |
| (e) | Cationic Polysaccharide | HYDROXYPROPYL GUAR HYDROXYPROPYLTRIMONIUM CHLORIDE | | 1 | 1 |
| (f) | Polar Oil | GLYCINE SOJA (SOYBEAN) OIL | | | 1 |
| (g) | Nonionic Emulsifier | PEG-40 HYDROGENATED CASTOR OIL | | | 1 |
| (h) | Misc. | SODIUM HYDROXIDE | ≤5 | ≤5 | ≤5 |
| (d) | WATER | | 95.8 | 94 | 92 |
| pH | | | 3-4 | 3-4 | 3-4 |

Example 2
(Conditioning Composition)

| | | | D |
|---|---|---|---|
| (a) | Cationic Surfactant | CETRIMONIUM CHLORIDE, BEHENTRIMONIUM CHLORIDE, AND BEHENTRIMONIUM METHOSULFATE | 3.1 |
| (b) | Fatty Compound | ZEA MAYS (CORN) GERM OIL, ISODODECANE, CAPRYLIC/CAPRIC TRIGLYCERIDE, LAURYL LAURATE, HYDROGENATED CASTOR OIL/SEBACIC ACID COPOLYMER, BIS-BEHENYL/ISOSTEARYL/PHYTOSTERYL DIMER DILINOLEYL DIMER DILINOLEATE, CETEARYL ALCOHOL | 4.5<br>6 |
| (c) | Silicone | AMODIMETHICONE AND AMINOPROPYL DIMETHICONE | 1.3 |
| (e) | Thickener | PVP AND HYDROXYPROPYL STARCH PHOSPHATE | 0.9 |
| (f) | Water Soluble Solvent | BUTYLENE GLYCOL AND ISOPROPYL ALCOHOL | 1.2 |
| (g) | Miscellaneous[1] | | ≤5 |
| (d) | WATER | | 80.8 |

[1]Vegetal extracts, composition colorants, pH adjusters, proteins or hydrolyzed proteins, fragrances, preservatives, actives, surfactants other than cationic surfactants, etc.

Example 3

Pre-Treatment with Fortifying Compositions

Testing was carried out to investigate how the compositions and methods described throughout the instant disclosure influence the integrity of oxidatively bleached or colored hair. Caucasian hair swatches (2 gm), curl pattern 4 (CP4), were cleansed with a standard shampoo prior to treatment. Bleaching compositions were prepared mixing a commercial bleach powder (9% hydrogen peroxide) and developer (30 Volume) in a ratio of 1:1.5 ratio (Bleach Powder:Developer (1:1.5)) with the ingredients listed below.

| Bleach Powder |
|---|
| Ingredients: potassium persulfate, sodium silicate, sodium stearate, magnesium carbonate hydroxide, ammonium persulfate, sodium metasilicate, Cyamopsis tetragonolobus gum/guar gum, paraffinum liquidum mineral oil, ultramarines, sodium lauryl sulfate, proline, threonine disodium, and EDTA |

| Developer (30 V) |
|---|
| Ingredients: aqua/water, hydrogen perioxide (9%), cetearyl alcohol, trideceth-2 carboxamide MEA, ceteareth-25, glycerin, tetrasodium etidronate, tetrasodium pyrophosphate, sodium silicate, phosphoric acid |

After cleansing the hair swatches were treated according to one of the following routines:

Control: Hair swatches were oxidatively bleached. A standard bleach powder and a developer (30V) were mixed in a ratio of 1:1.5 ratio (Bleach Powder:Developer (1:1.5)) to preparing the bleaching composition. 10 grams of the hair bleaching composition was applied to each hair swatch. The hair bleaching composition was allowed to remain on the hair for 50 minutes. After 50 minutes, the hair bleaching composition was rinsed from the hair and the hair was again cleansed with the standard shampoo. Bleached hair swatches not subjected to any additional treatments served as a control.

Comparative 1: Hair swatches were treated as described above for the control. However, after cleansing the bleached hair with the standard shampoo (and rinsing the shampoo from the hair), the conditioning composition of Example 2 was immediately applied to the wet or damp hair and allowed to remain on the hair for 5 minutes. After 5 minutes, the conditioning composition was rinsed from the hair.

Inventive A: Before oxidatively bleaching, the hair swatches were pre-treated with Inventive Fortifying Composition A from Example 1. Inventive Fortifying Composition A was applied to the hair swatches (0.4 g per gram of hair), messaged into the hair swatches for 1 minute and allowed to remain on the hair swatches for an additional 5 minutes. Immediately after the additional 5 minutes, the hair swatches were bleached as described for the control. after cleansing the bleached hair with the standard shampoo (and rinsing the shampoo from the hair), the conditioning composition of Example 2 was immediately applied to the wet or damp hair and allowed to remain on the hair for 5 minutes. After 5 minutes, the conditioning composition was rinsed from the hair.

Inventive B: Before oxidatively bleaching the hair, the hair swatches were pre-treated with Inventive Fortifying Composition B from Example 1. Inventive Fortifying Composition B was applied to the hair swatches (0.4 g per gram of hair), messaged into the hair swatches for 1 minute and allowed to remain on the hair swatches for an additional 5 minutes. Immediately after the additional 5 minutes, the hair swatches were bleached as described for the control. after cleansing the bleached hair with the standard shampoo (and rinsing the shampoo from the hair), the conditioning composition of Example 2 was immediately applied to the wet or damp hair and allowed to remain on the hair for 5 minutes. After 5 minutes, the conditioning composition was rinsed from the hair.

Inventive C: Before oxidatively bleaching the hair, the hair swatches were pre-treated with Inventive Fortifying Composition B from Example 1. Inventive Fortifying Composition B was applied to the hair swatches (0.4 g per gram of hair), messaged into the hair swatches for 1 minute and allowed to remain on the hair swatches for an additional 5 minutes. Immediately after the additional 5 minutes, the hair swatches were bleached as described for the control. after cleansing the bleached hair with the standard shampoo (and rinsing the shampoo from the hair), the conditioning composition of Example 2 was immediately applied to the wet or damp hair and allowed to remain on the hair for 5 minutes. After 5 minutes, the conditioning composition was rinsed from the hair.

Hair treated according to the protocols described above was analyzed with miniature tensile testing (Young's Modulus and Break Stress) and with differential scanning calorimetry (Thermal Integrity). One-way ANOVA analysis, using SPSS software at 95% confidence interval was used to analyze significant differences in DSC and MTT outputs. The frizz of hair was also evaluated.

Elastic Modulus and Break Stress

The hair was analyzed with miniature tensile testing (Miniature Tensile Tester, MTT-675, Dia-Stron Ltd). MTT is used to measure Young's Modulus, i.e., slope of the initial portion of the stress-strain curve, which is adjusted for cross-sectional area, representing a measure of the hair spring-like structure. It also measures break stress, which is the total force needed to break hair fiber. Test results were subjected to statistical analysis using Tukey-Kramer post-hoc tests, IBM SPSS software, with k=3, to determine and exclude significant outliers. Statistical significance was analyzed using SPSS software at 95% confidence. The results are presented in the table below and the corresponding figures. Elastic modulus represents elastic properties of the fiber. Higher values represent higher elasticity, indicating the hair is less brittle due to fortification and lack of dryness and damage.

| MTT Results | | | | | |
|---|---|---|---|---|---|
| | Control | C-1 | I-A | I-B | I-C |
| Elastic modulus (MPa) | 1072 ± 192 | 1021 ± 274 | 1213 ± 142 | 1660 ± 316 | 1244 ± 121 |
| Statistical Significance ($p \leq 0.05$) | a | a | b | c | b |

-continued

| MTT Results | | | | | |
|---|---|---|---|---|---|
| | Control | C-1 | I-A | I-B | I-C |
| Break Stress (MPa) | 131 ± 24 | 136 ± 22 | 148 ± 15 | 178 ± 27 | 148 ± 19 |
| Statistical Significance ($p \le 0.05$) | a | a | b | c | b |

The elastic modulus statistical significance is as follows: I-B>I-A=I-C>Control=C-1. The break stress statistical significance is as follows: I-B>I-A=I-C>Control=C-1. The data show that inventive routine B performed better than inventive routines A and C; and that inventive routines A and C performed better than the control and the comparative routine 1.

Thermal Integrity/Protein Cross-link Density

The hair was analyzed with differential scanning calorimetry (DSC, DSC-2500, TA Instruments). DSC is used to measure denaturation temperature, which is a measure of the thermal stability of proteins in hair and a representation of the protein cross-link density. Higher values represent higher thermal integrity, which is an indication of more crosslinking (stronger hair).

| DSC Results | | | | | |
|---|---|---|---|---|---|
| | Control | C-1 | I-A | I-B | I-C |
| Cross-Link Density (° C.) Mean ± std. dev. | 143.8 ± 0.1 | 146.9 ± 0.2 | 155.9 ± 0.1 | 151.1 ± 0.2 | 155 ± 0.3 |
| Statistical Significance ($p \le 0.05$) | a | b | d | c | d |

Cross-link density statistical significance is as follows: I-A=I-C>I-B>C-1>Control. Inventive routines I-A and I-C performed better than inventive routine I-B; and inventive routine I-B performed better than comparative routine C-1, which performed better than control.

Frizz Testing

Swatches treated according to the protocols outlined above were placed in a humidity chamber at 25° C. and 80% relative humidity. After 4 hours, the swatches were removed from the humidity chamber and visually analyzed. Pictures of the hair swatches are shown in FIG. 1. The results show that hair pre-treated with the fortifying compositions of Example 1 suffered less frizz and maintained better shape and curls.

Example 6

Post-Treatment with Fortifying Compositions

Testing was carried out to investigate how the compositions and methods described throughout the instant disclosure influence the integrity of oxidatively bleached or colored hair. Caucasian hair swatches (2 gm), curl pattern 4 (CP4), were cleansed with a standard shampoo prior to treatment. Bleaching compositions were prepared mixing a commercial bleach powder (9% hydrogen peroxide) and developer (30 Volume) in a ratio of 1:1.5 ratio (Bleach Powder:Developer (1:1.5)) with the ingredients listed below.

| Bleach Powder |
|---|
| potassium persulfate, sodium silicate, sodium stearate, magnesium carbonate hydroxide, ammonium persulfate, sodium metasilicate, Cyamopsis tetragonolobus gum/guar gum, paraffmum liquidum mineral oil, ultramarines. Sodium lauryl sulfate, proline. Threonine disodium EDTA |

| Developer (30 V) |
|---|
| Aqua/Water, Hydrogen peroxide (9%), cetearyl alcohol, Trideceth-2 carboxamide MEA, Ceteareth-25, Glycerin, Tetrasodium etidronate, tetrasodium Pyrophosphate, Sodium silicate, phosphoric acid |

After cleansing the hair swatches were treated according to one of the following routines:

Control: Hair swatches were oxidatively bleached. A standard bleach powder and a developer (30V) were mixed in a ratio of 1:1.5 ratio (Bleach Powder:Developer (1:1.5)) to preparing the bleaching composition. 10 grams of the hair bleaching composition was applied to each hair swatch. The hair bleaching composition was allowed to remain on the hair for 50 minutes. After 50 minutes, the hair bleaching composition was rinsed from the hair and the hair was cleansed with a shampoo. Bleached hair swatches not subjected to any additional treatments served as a control.

Comparative 1: Hair swatches were bleached as described above for the control.

However, after cleansing the bleached hair with the shampoo (and rinsing the shampoo from the hair), the conditioning composition of Example 2 was immediately applied to the wet or damp hair and allowed to remain on the hair for 5 minutes. After 5 minutes, the conditioning composition was rinsed from the hair.

Inventive A: Hair swatches were bleached as described above for the control. However, after cleansing the bleached hair with the shampoo (and rinsing the shampoo from the hair), Inventive Fortifying Composition A was applied to the hair swatches (0.4 g per gram of hair), messaged into the hair swatches for 1 minute, and allowed to remain on the hair swatches for an additional 5 minutes. After the additional 5 minutes, the hair swatches were cleansed with a standard shampoo and the shampoo rinsed from the hair. Immediately after rinsing the shampoo from the hair, Inventive Fortifying Composition A was applied to the hair swatches (0.4 g per gram of hair) again (a second time), messaged into the hair swatches for 1 minute and allowed to remain on the hair swatches for an additional 5 minutes. Immediately after the additional 5 minutes, without rinsing Inventive Fortifying Composition A from the hair, the conditioning composition of Example 2 was applied to the hair, allowed to remain on the hair for 5 minutes, and rinsed from the hair.

Inventive B: Hair swatches were bleached as described above for the control. However, after cleansing the bleached hair with the shampoo (and rinsing the shampoo from the hair), Inventive Fortifying Composition B of Example 1 was applied to the hair swatches (0.4 g per gram of hair), messaged into the hair swatches for 1 minute, and allowed to remain on the hair swatches for an additional 5 minutes. Immediately after the additional 5 minutes, the hair swatches were cleansed with a standard shampoo and the shampoo rinsed from the hair. Immediately after rinsing the shampoo from the hair, Inventive Fortifying Composition B was applied to the hair swatches (0.4 g per gram of hair) again (a second time), messaged into the hair swatches for 1 minute and allowed to remain on the hair swatches for an additional 5 minutes. Immediately after the additional 5 minutes, without rinsing Inventive Fortifying Composition B from the hair, the conditioning composition of Example 2 was applied to the hair, allowed to remain on the hair for 5 minutes, and rinsed from the hair.

Inventive C: Hair swatches were bleached as described above for the control. However, after cleansing the bleached hair with the shampoo (and rinsing the shampoo from the hair), Inventive Fortifying Composition C of Example 1 was applied to the hair swatches (0.4 g per gram of hair), messaged into the hair swatches for 1 minute, and allowed to remain on the hair swatches for an additional 5 minutes. Immediately after the additional 5 minutes, the hair swatches were cleansed with a standard shampoo and the shampoo rinsed from the hair. Immediately after rinsing the shampoo from the hair, Inventive Fortifying Composition C was applied to the hair swatches (0.4 g per gram of hair) again (a second time), messaged into the hair swatches for 1 minute and allowed to remain on the hair swatches for an additional 5 minutes. Immediately after the additional 5 minutes, without rinsing Inventive Fortifying Composition C from the hair, the conditioning composition of Example 2 was applied to the hair, allowed to remain on the hair for 5 minutes, and rinsed from the hair Hair treated according to the protocols described above was analyzed with miniature tensile testing (Elastic Modulus and Break Stress) and with differential scanning calorimetry (Thermal Integrity). One-way ANOVA analysis was used to determined statistical significance among control and inventive composition at 95% confidence. The frizz of hair was also evaluated.

Elastic Modulus and Break Stress

The hair was analyzed with miniature tensile testing (Miniature Tensile Tester, MTT-675, Dia-Stron Ltd). MTT is used to measure elastic modulus. It also measures break stress, which is the total force needed to break hair fiber. Test results were subjected to statistical analysis using Tukey-Kramer post-hoc tests with IBM SPSS statistical analysis software. One-way ANOVA analysis was used to determined statistical significance among control and inventive composition. The results are presented in the table below and the corresponding figures. Elastic modulus represents elasticity. Higher values represent higher elasticity, indicating the hair is less brittle due to fortification and lack of dryness and damage.

| MTT Results | | | | | |
|---|---|---|---|---|---|
| | Control | C-1 | I-A | I-B | I-C |
| Elastic Modulus (MPa) | 1072 ± 192 | 1021 ± 274 | 1281 ± 240 | 1810 ± 493 | 1255 ± 278 |
| Statistical Significance ($p \leq 0.05$) | a | a | b | c | b |
| Break Stress | 131 ± 24 | 136 ± 22 | 146 ± 15 | 183 ± 22 | 146 ± 16 |
| Statistical Significance ($p \leq 0.05$) | a | a | b | c | b |

The elastic modulus statistical significance is as follows: I-B>I-A=I-C>Control=C-1. The break stress statical significance is as follows: I-B>I-A=I-C>Control=C-1. Thus inventive routine B performed better than inventive routines I-A and I-C; and inventive routines I-A and I-C performed better than control.

The hair was analyzed with differential scanning calorimetry (DSC, DSC-2500, TA Instruments). DSC is used to measure denaturation temperature, which is a measure of the thermal stability of proteins in hair and a representation of cross-link density. Higher values represent higher thermal integrity, which is an indication of more crosslinking formation with hair bonds (stronger hair).

| DSC Results | | | | | |
|---|---|---|---|---|---|
| | Control | C-1 | I-A | I-B | I-C |
| Cross-Link Density (° C.) | 143.8 ± 0.1 | 146.9 ± 0.2 | 159.3 ± 0.1 | 157.7 ± 0.2 | 157.8 ± 0.1 |
| Statistical Significance ($p \leq 0.05$) | a | b | d | c | c |

The cross-link density statistical significance is as follows: I-A>I-B=I-C>C-1>Control. Thus, inventive routine I-A performed better than inventive routines I-B and I-C; and inventive routines I-B and I-C performed better than comparative routine 1, which performed better than the control.

Frizz Testing

Figure 2:
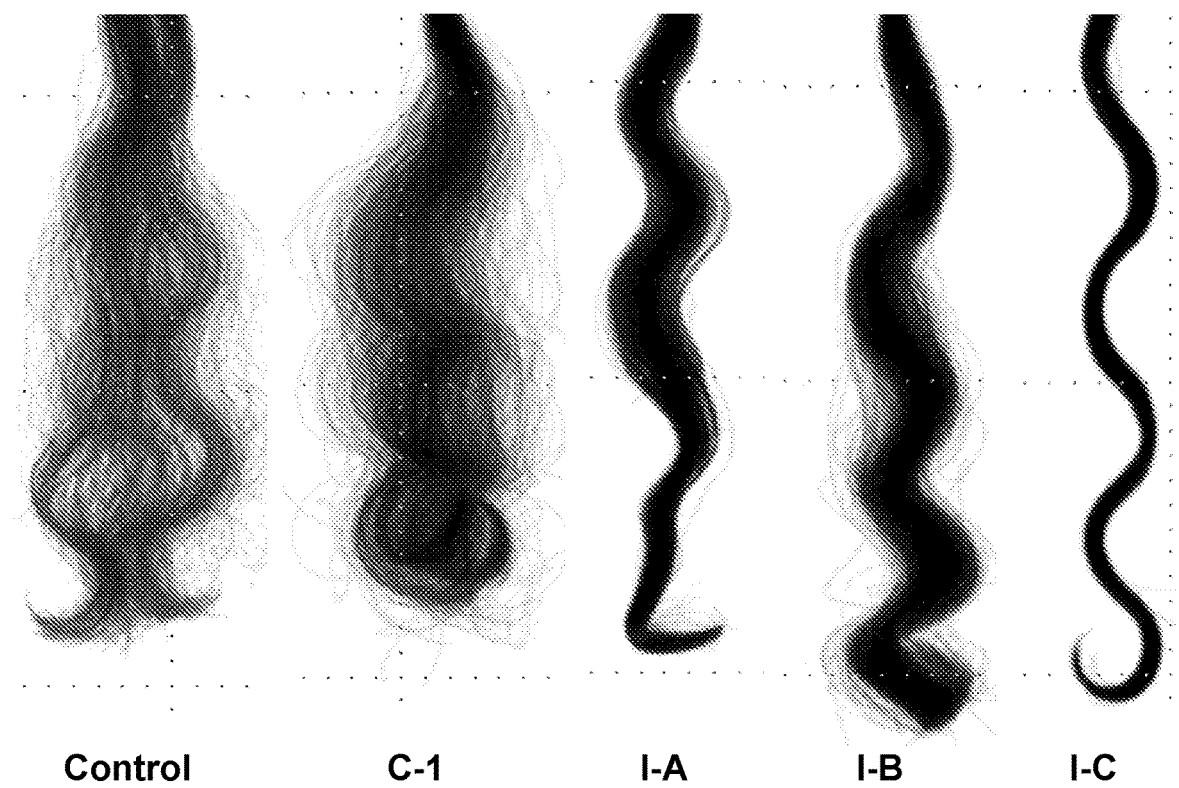
FIG. 2 shows hair swatches treated according to the instant disclosure and hair swatches treated with comparative routines after being subjected to a humidity treatment.

Swatches treated according to the protocols outlined above were placed in a humidity chamber at 25° C. and 80% relative humidity. After 4 hours, the swatches were removed from the humidity chamber and visually analyzed. Pictures of the hair swatches are shown in FIG. 2. The results show that hair pre-treated with the fortifying compositions of Example 1 suffered less frizz and maintained better shape and curls.

The foregoing description illustrates and describes the disclosure. Additionally, the disclosure shows and describes only the preferred embodiments. However, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting. Appropriate counterions for the components described herein are known in the art.

The expression "one or more" means "at least one" and thus includes individual components as well as mixtures/combinations.

The term "plurality" means "more than one" or "two or more." Other than in the operating examples, or where otherwise indicated, all numbers expressing quantities of ingredients and/or reaction conditions may be modified in all instances by the term "about," meaning within +/−5% of the indicated number.

All percentages, parts and ratios herein are based upon the total weight of the compositions of the present invention, unless otherwise indicated.

Some of the various categories of components identified may overlap. In such cases where overlap may exist and the composition includes both components (or the composition includes more than two components that overlap), an overlapping compound does not represent more than one component. For example, certain compounds may be considered both a nonionic surfactant or emulsifier and a fatty compound. If a particular composition includes both a nonionic surfactant or emulsifier and a fatty compound, a single compound will serve as only the nonionic surfactant or emulsifier or only as the fatty compound (the single compound does not simultaneously serve as both the nonionic surfactant or emulsifier and the fatty component).

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The compositions of the instant case may optionally include one or more surfactants and/or emulsifiers other than the nonionic surfactant and emulsifiers described above, for example, one or more anionic, cationic, and/or amphoteric/zwitterionic surfactants.

The term "surfactants" and "emulsifiers" include salts of the surfactants and emulsifiers even if not explicitly stated. In other words, whenever the disclosure refers to a surfactant or emulsifier, it is intended that salts are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants and emulsifiers. However, additional cations such as ammonium ions, or alkanolammonium ions such as monoethanolammonium or triethanolammonium ions, may also form salts of surfactants.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

All components that are positively set forth in the instant disclosure may be negatively excluded from the claims, e.g., a claimed composition may be "free," "essentially free" (or "substantially free") of one or more components that are positively set forth in the instant disclosure. Furthermore, components, compounds, or ingredients described for use in the fortifying composition may be excluded from the conditioning compositions, and vice versa.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for protecting hair and mitigating damage to the hair from oxidative bleaching or coloring of the hair, the method comprising:
  (i) applying a fortifying composition to hair to be oxidatively bleached or colored and allowing the fortifying composition to remain on the hair for a first period of time, the fortifying composition comprising:
    (a) citric acid;
    (b) cyclodextrin;
      wherein a combined total amount of (i)(a) and (i)(b) is about 2 to about 15 wt. %;
    (c) one or more polyols having from 2 to 10 carbon atoms; and
    (d) water;
      wherein all weight percentages of (i) are based on a total weight of the fortifying composition;
  (ii) upon expiration of the first period of time, without rinsing the fortifying composition from the hair, applying an oxidative bleaching or coloring composition to the hair and oxidatively bleaching or coloring the hair;
  (iii) after oxidatively bleaching or coloring the hair, cleansing the hair with a shampoo to remove the oxidative bleaching or coloring composition from the hair;
  (iv) after rinsing the shampoo from the hair, applying a conditioning composition to the hair and allowing the conditioning composition to remain on the hair for a second period of time, the conditioning composition comprising;
    (a) one or more cationic surfactants;
    (b) one or more non-silicone based fatty compounds;
    (c) one or more silicones; and
    (d) water; and
  (v) upon expiration of the second period of time, rinsing the conditioning composition from the hair upon expiration of the second period of time.

2. The method of claim 1, wherein the fortifying composition has a pH of about 2 to about 6.

3. The method of claim 1, wherein the citric acid of (i)(a) and cyclodextrin of (i)(b) are in a mole ratio of about 20:1 to about 3:1 ((a):(b)).

4. The method of claim 1, wherein the one or more polyols having from 2 to 10 carbon atoms are selected from ethylene glycol, propylene glycol, butylene glycol, hexylene glycol, pentylene glycol, diethylene glycol, dipropylene glycol, 1,3 propanediol, glycerin, or combinations thereof.

5. The method of claim 4, wherein at least one of the one or more polyols having from 2 to 10 carbon atoms is glycerin.

6. The method of claim 1, wherein the fortifying composition further comprises:
 (e) one or more cationic polysaccharides;
 (f) one or more polar oils; and/or
 (g) one or more nonionic emulsifiers.

7. The method of claim 6 comprising the one or more cationic polysaccharides, wherein at least one of the one or more cationic polysaccharides is a cationic guar.

8. The method of claim 6 comprising the one or more nonionic emulsifiers, wherein at least one of the one or more nonionic emulsifiers is an alkoxylated nonionic emulsifier.

9. The method of claim 1, wherein the method comprises:
 (i) applying a fortifying composition to hair to be oxidatively bleached or colored and allowing the fortifying composition to remain on the hair for a first period of time of about 1 to about 30 minutes, the fortifying composition comprising:
  (a) about 1 to about 10 wt. % of citric acid;
  (b) about 0.5 to about 10 wt. % of cyclodextrin;
   wherein a combined total amount of (a) and (b) is about 2 to about 15 wt. %;
  (c) about 0.1 to about 10 wt. % of one or more polyols having from 2 to 10 carbon atoms;
  (d) about 60 to about 96 wt. % of water;
  (e) optionally, about 0.1 to about 5 wt. % of one or more cationic polysaccharides;
  (f) optionally, about 0.1 to about 8 wt. % of one or more polar oils;
  (g) optionally, about 0.1 to about 8 wt. % of one or more nonionic emulsifiers; and
  (h) optionally, about 0.1 to about 10 wt. % of one or more miscellaneous ingredients;
   wherein all weight percentages of (i) are based on a total weight of the fortifying composition;
 (ii) upon expiration of the first period of time, without rinsing the fortifying composition from the hair, applying an oxidative bleaching or coloring composition to the hair and oxidatively bleaching or coloring the hair;
 (iii) after oxidatively bleaching or coloring the hair, cleansing the hair with a shampoo to remove the oxidative bleaching or coloring composition from the hair;
 (iv) within about 30 minutes from rinsing the shampoo from the hair, applying a conditioning composition to the hair for a second period of time of about 1 to 30 minutes, the conditioning composition comprising;
  (a) about 0.5 to about 10 wt. % of one or more cationic surfactants, based on a total weight of the conditioning composition;
  (b) about 1 to about 30 wt. % of one or more fatty compounds, based on a total weight of the conditioning composition;
  (c) about 0.1 to about 5 wt. % of one or more amino-functionalized silicones;
  (d) 60 to about 90 wt. % of water, based on a total weight of the conditioning composition;
  (e) optionally, about 0.1 to about 8 wt. % of one or more thickening agents;
  (f) optionally, about 0.1 to about 8 wt. % of one or more water soluble solvents; and
  (g) optionally, about 0.1 to about 10 wt. % of one or more miscellaneous ingredients;
   wherein all weight percentages of (iv) are based on a total weight of the conditioning composition; and
 (v) upon expiration of the second period of time, rinsing the conditioning composition from the hair.

10. The method of claim 1, wherein the method strengthens the hair, improves curl retention of the hair, prevents frizz of the hair, and remediates damage to the hair caused by the chemical bleaching or coloring of the hair to a greater extent than A carrying out the method without the fortifying composition.

11. A method for protecting hair and mitigating damage to the hair from oxidative bleaching or coloring of the hair, the method comprising:
 (i) applying an oxidative bleaching or coloring composition to the hair and oxidatively bleaching or coloring the hair followed by cleansing the hair with a shampoo to remove the oxidative bleaching or coloring composition from the hair;
 (ii) after rinsing the shampoo from the hair, applying a first application of a fortifying composition to the hair, and allowing the first application of the fortifying composition to remain on the hair for a first period of time, the fortifying composition comprising:
  (a) citric acid;
  (b) cyclodextrin;
   wherein a combined total amount of (i)(a) and (i)(b) is about 2 to about 15 wt. %;
  (c) one or more polyols having from 2 to 10 carbon atoms; and
  (d) water;
   wherein all weight percentages of (ii) are based on a total weight of the fortifying composition;
 (iii) upon expiration of the first period of time, cleansing the hair with a shampoo;
 (iv) after rinsing the shampoo from the hair, applying a second application of the fortifying composition to the hair and allowing the second application of the fortifying composition to remain on the hair for a second period of time;
 (v) upon expiration of the second period of time, without rinsing the second application of the fortifying composition from the hair, applying a conditioning composition to the hair and allowing the conditioning composition to remain on the hair for a third period of time, the conditioning composition comprising:
  (a) one or more cationic surfactants;
  (b) one or more non-silicone based fatty compounds;
  (c) one or more silicones; and
  (d) water; and
 (vi) upon expiration of the third period of time, rinsing the fortifying composition and the conditioning composition from the hair.

12. The method of claim 11, wherein the fortifying composition has a pH of about 2 to about 6.

13. The method of claim 11, wherein the citric acid of (i)(a) and cyclodextrin of (i)(b) are in a mole ratio of about 20:1 to about 3:1 ((a):(b)).

14. The method of claim 11, wherein the one or more polyols having from 2 to 10 carbon atoms are selected from ethylene glycol, propylene glycol, butylene glycol, hexylene glycol, pentylene glycol, diethylene glycol, dipropylene glycol, 1,3 propanediol, glycerin, or combinations thereof.

15. The method of claim 14, wherein at least one of the one or more polyols having from 2 to 10 carbon atoms is glycerin.

16. The method of claim 11, wherein the fortifying composition further comprises:
   (d) optionally, one or more cationic polysaccharides;
   (f) one or more polar oils; and/or
   (g) one or more nonionic emulsifiers.

17. The method of claim 16 comprising the one or more cationic polysaccharides, wherein at least one of the one or more cationic polysaccharides is a cationic guar.

18. The method of claim 16 comprising the one or more nonionic emulsifiers, wherein at least one of the one or more nonionic emulsifiers is an alkoxylated nonionic emulsifier.

19. The method of claim 11, wherein the method comprises:
   (i) applying an oxidative bleaching or coloring composition to the hair and oxidatively bleaching or coloring the hair followed by cleansing the hair with a shampoo to remove the oxidative bleaching or coloring composition from the hair;
   (ii) within about 30 minutes from rinsing the shampoo from the hair, applying a first application of a fortifying composition to the hair and allowing the first application of the fortifying composition to remain on the hair for a first period of time of about 1 to about 30 minutes, the fortifying composition comprising:
      (a) about 1 to about 10 wt. % of citric acid;
      (b) about 0.5 to about 10 wt. % of cyclodextrin;
         wherein a combined total amount of (a) and (b) is about 2 to about 15 wt. %;
      (c) about 0.1 to about 10 wt. % of one or more polyols having from 2 to 10 carbon atoms;
      (d) about 60 to about 96 wt. % of water;
      (e) optionally, about 0.1 to about 5 wt. % of one or more cationic polysaccharides;
      (f) optionally, about 0.1 to about 8 wt. % of one or more polar oils;
      (g) optionally, about 0.1 to about 8 wt. % of one or more nonionic emulsifiers; and
      (h) optionally, about 0.1 to about 10 wt. % of one or more miscellaneous ingredients;
      wherein all weight percentages of (ii) are based on a total weight of the fortifying composition;
   (iii) upon expiration of the first period of time, without rinsing the fortifying composition from the hair, applying a shampoo composition to the hair and cleansing the hair;
   (iv) within about 30 minutes from rinsing the shampoo composition from the hair, applying a second application of the fortifying composition to the hair and allowing the second application of the fortifying composition to remain on the hair for a second period of time of about 1 to about 30 minutes;
   (v) upon expiration of the second period of time, without rinsing the second application of the fortifying composition from the hair, applying a conditioning composition to the hair and allowing the conditioning composition to remain on the hair for a third period of time of about 1 to about 30 minutes, the conditioning composition comprising:
      (a) about 0.5 to about 10 wt. % of one or more cationic surfactants, based on a total weight of the conditioning composition;
      (b) about 1 to about 30 wt. % of one or more fatty compounds, based on a total weight of the conditioning composition;
      (c) about 0.1 to about 5 wt. % of one or more amino-functionalized silicones;
      (d) 60 to about 90 wt. % of water, based on a total weight of the conditioning composition;
      (e) optionally, about 0.1 to about 8 wt. % of one or more thickening agents;
      (f) optionally, about 0.1 to about 8 wt. % of one or more water soluble solvents; and
      (g) optionally, about 0.1 to about 10 wt. % of one or more miscellaneous ingredients;
      wherein all weight percentages of (iii) are based on a total weight of the conditioning composition; and
   (vi) upon expiration of the third period of time, rinsing the fortifying composition and the conditioning composition from the hair.

20. The method of claim 11, wherein the method strengthens the hair, improves curl retention of the hair, prevents frizz of the hair, and remediates damage to the hair caused by the chemical bleaching or coloring of the hair to a greater extent than carrying out the method without the first application and/or the second application of the fortifying composition to the hair.

* * * * *